US007208467B2

(12) United States Patent
Krieger et al.

(10) Patent No.: US 7,208,467 B2
(45) Date of Patent: Apr. 24, 2007

(54) LIPID-ALTERING COMPOSITIONS FOR THE TREATMENT OF INFERTILITY

(76) Inventors: Monty Krieger, 33 Woodbine Cir., Needham, MA (US) 02494; Helena E. Miettinen, Merikorttie 13A 425, Helsinki 96 (FI) 00960

( * ) Notice: Subject to any disclaimer, the term of this patent is extended or adjusted under 35 U.S.C. 154(b) by 560 days.

(21) Appl. No.: 10/164,863

(22) Filed: Jun. 7, 2002

(65) Prior Publication Data
US 2003/0232879 A1 Dec. 18, 2003

(51) Int. Cl.
*A01N 37/18* (2006.01)
*A01N 43/16* (2006.01)
*A01N 43/08* (2006.01)
*A01N 31/00* (2006.01)
*A61K 38/00* (2006.01)

(52) U.S. Cl. .................. 514/2; 514/458; 514/470; 514/474; 514/706

(58) Field of Classification Search .............. 514/2
See application file for complete search history.

(56) References Cited

U.S. PATENT DOCUMENTS

| | | | |
|---|---|---|---|
| 3,625,214 A | 12/1971 | Higuchi | |
| 4,244,946 A | 1/1981 | River et al. | |
| 4,305,872 A | 12/1981 | Johnston et al. | |
| 4,316,891 A | 2/1982 | Guillemin et al. | |
| 4,629,784 A | 12/1986 | Stammer | |
| 4,789,734 A | 12/1988 | Pierschbacher | |
| 4,792,525 A | 12/1988 | Ruoslaghti et al. | |
| 4,868,116 A | 9/1989 | Morgan et al. | |
| 4,906,474 A | 3/1990 | Langer et al. | |
| 4,925,673 A | 5/1990 | Steiner et al. | |
| 4,980,286 A | 12/1990 | Morgan et al. | |
| 5,674,488 A | 10/1997 | Reich | |
| 5,962,322 A | 10/1999 | Kozarsky et al. | |
| 5,965,790 A | * | 10/1999 | Acton |
| 6,121,319 A | 9/2000 | Somers | |
| 2002/0016364 A1 | 2/2002 | Luchoomun et al. | |
| 2002/0099040 A1 | 7/2002 | Krieger | |

FOREIGN PATENT DOCUMENTS

| WO | WO 93/01286 | 1/1993 |
|---|---|---|
| WO | WO 96/00288 | 1/1996 |
| WO | WO 97/18304 | 5/1997 |

OTHER PUBLICATIONS

Bertolotti M et al. J. Lipid Research. 37:1812-1822, 1996.*
Abumrad, et al., "Cloning of a Rat Adipocyte Membrane Protein Implicated in Binding or Transport of Long-chain Fatty Acids That Is Induced during Preadipocyte Differentiation," *J. Biol. Chem.* 268:17665-17668 (1993).
Acton, et al., "Expression Cloning of SR-BI, a CD36-related Class B Scavenger Receptor," *J. Biol. Chem.* 269(33): 21003-21009 (1994).
Acton, et al., "The Collagenous Domains of Macrophage Scavenger Receptors and Complement Component C1q Mediate Their Similar, But Not Identical, Binding Specificities for Polyanionic Ligands," *J. Biol. Chem.* 268: 3530-3537 (1993).
Acton, et al., "Identification of scavenger receptor SR-BI as a high density lipoprotein receptor," *Science* 271: 518-520 (1996).
Agrawal, et al., "Oligodeoxynucleoside phosphoramidates and phosphorothioates as inhibitors of human immunodeficiency virus," *Proc. Natl. Acad. Sci. USA*, 85:7079-7083 (1988).
Arai, et al., "Multiple Receptors for Modified Low Density Lipoproteins in Mouse Peritoneal Macrophages: Different Uptake Mechanisms for Acetylated and Oxidized Low Density Lipoproteins," *Biochem. Biophys. Res. Commun* 159:1375-1382 (1989).
Asch, et al., "Isolation of the Thrombospondin Membrane Receptor," *J. Clin. Invest.* 79:1054-1061 (1987).
Askew, et al., "Molecular Recognition with Convergent Functional Groups, Synthetic and Structural Studies with a Model Receptor for Nucleic Acid Components", *J. Am. Chem. Soc.* 111: 1082-1090 (1989).
Bajetta, et al., "Endocrinological and clinical evaluation of two doses of formestane in advanced breast cancer," *Br. J. Cancer* 70: 145-150 (1994).
Baldini, et al., "Cloning of a Rab3 Isotype Predominately Expressed in Adipocytes", *Proc. Natl. Acad. Sci. U.S.A.* 89: 5049-5052 (1992).
Bickel, et al., "Rabbit Aortic Smooth Muscle Cells Express Inducible Macrophage Scavenger Receptor Messenger RNA that is Absent from Endothelial Cells", *J. Clin. Invest.* 90: 1450-1457 (1992).

(Continued)

*Primary Examiner*—Robert S. Landsman
(74) *Attorney, Agent, or Firm*—Pabst Patent Group LLP

(57) ABSTRACT

SR-BI is present at relatively high levels on the membranes of hepatocytes and steroidogenic tissues, including the adrenal gland, testes, and ovaries, where it mediates the uptake and transport of cholesteryl ester from high density lipoproteins. It has been demonstrated that transgenic animals which do not produce SR-BI are healthy, with the exception that the females are infertile. SR-BI KO females have abnormal HDLs, ovulate dysfunctional oocytes and are infertile. Surgical, genetic and pharmacologic methods were used to show that the fertility of SR-BI KO females (or their transplanted oocytes) can be restored in the absence of ovarian and/or extraovarian SR-BI expression by manipulations that modify the structure, composition and/or abundance of their abnormal plasma lipoproteins. These manipulations included inactivation of the apolipoprotein A-I gene and administration of the cholesterol-lowering drug PROBUCOL™. In the absence of treatment, female animals which do not express SR-BI have dramatically reduced levels of offspring, even though they are otherwise healthy and the males normal. Studies demonstrate that they do not produce viable eggs and have a defect involving implantation of normal eggs.

15 Claims, 2 Drawing Sheets

OTHER PUBLICATIONS

Blume, et al., "Triple Helix Formation by Purine-rich Oligonucleotides Targeted to the Human Dihydrofolate Reductase Promoter", *Nucl. Acids Res.* 20: 1777-1784 (1992).

Bork, et al., "Go hunting in sequence databases but watch out for the traps," *Trends in Genetics* 12: 425-427 (1996).

Bork, et al., "Powers and pitfalls in sequence analysis: the 70% hurdle," *Genome Research* 10: 398-400 (2000).

Brenner,"Errors in genome annotation," *Trends in Genetics* 15: 132-133 (1999).

Brown & Goldstein, "Lipoprotein Metabolism In The Macrophage: Implications for Cholesterol Deposition in Atherosclerosis" *Annu. Rev. Biochem.* 52: 223-261 (1983).

Calvo & Vega, "Identification, Primary Structure, and Distribution of CLA-1, a Novel Member of the CD36/LIMPII Gene Family", *J. Biol. Chem.* 268: 18929:18935 (1993).

Charron, et al., "A Glucose Transport Protein Expressed Predominately in Insulin-responsive Tissues", *Proc. Natl. Acad. Sci. U.S.A.* 86: 2535-2539 (1989).

Cirkel, et al., "Medical treatment of symptomatic endometriosis," *Human Reproduction* 11: 89-101 (1996).

Cooney, et al., "Site-Specfic Oligonucleotide Binding Represses Transcription of the Human c-myc Gene in Vitro," *Science* 241: 456-459 (1988).

Crooke, "Progress Toward Oligonucleotide Therapeutics: Pharmacodynamic Properties", *FASEB J.* 7: 533-539 (1993).

Doerks, et al., "Protein annotation: detective work for function prediction," *Trends in Genetics* 14: 248-250 ( 1998).

Doi, et al., "Charged Collagen Struture Mediates the Recognition of Negatively Charged Macromolecules by Macrophage Scavenger Receptors," *J. Biol. Chem.* 268: 2126-2133 (1993).

Duval-Valentin, et al., "Specific Inhibition of Transcription by Triple Helix-Forming Oligonucleotides," *Proc. Natl. Acad. Sci. USA*, 89: 504-508 (1992).

Endemann, et al. "CD36 Is a Receptor for Oxidized Low Density Lipoprotein", *J. Biol. Chem.* 268: 11811-11816 (1993).

Fraser, et al., "Divalent cation-independent macrophage adhesion inhibited by monoclonal antibody to murine scavenger receptor," *Nature* 364: 343-346 (1993).

Freeman, et al., "Expression of type I and type II bovine scavenger receptors in Chinese hamster ovary cells: Lipid droplet accumulation and nonreciprocal cross competition by acetylated and oxidized low density lipoprotein", *Proc. Natl. Acad. Sci. U.S.A.* 88: 4931-4935 (1991).

Glass, et al., "Dissociation of tissue uptake of cholesterol ester from that of apoprotein A-I of rat plasma high density lipoprotein: selective delivery of cholesterol ester to liver, adrenal, and gonad," *Proc. Natl. Acad. Sci. USA* 80: 5435 (1983).

Goldstein, et al., "Binding site on macrophages that mediates uptake and degradation of acetylated low density lipoprotein, producing massive cholesterol deposition", *Proc. Natl. Acad. Sci. U.S.A.* 76: 333-337 (1979).

Greenwalt, et al., "Membrane Glycoprotein CD36: A Review of Its Roles in Adherence, Signal Transduction, and Transfusion Medicine", *Blood* 80:1105-1115 (1992).

Gregoriadis, Chapter 14: "Liposomes", *Drug Carriers in Biology and Medicine* Academic Press, pp. 287-341 (1979).

Grigoriev, et al., "A Triple Helix-forming Oligonucleotide-Intercalator Conjugate Acts as a Transcriptional Repressor via Inhibition of NF KB Binding to Interleukin-2 Receptor α-Regulatory Sequence", *J. Biol. Chem.* 267: 3389-3395 (1992).

Haberland, et al., "Two Distinct Receptors Account for Recognition of Maleyl-Albumin in Human Monocytes during Differentiation In Vitro", *J. Clin. Inves.* 77: 681-689 (1986).

Herz, et al., "Surface location and high affinity for calcium of a 500-kd liver membrane protein closely related to the LDL-receptor suggest a physiological role as lipoprotein receptor", *EMBO J.* 7: 4119-4127 (1988).

Holt, et al., "An Oligomer Complementary to c-myc mRNA Inhibits Proliferation of HL-60 Promyelocytic Cells and Induces Differentiation", *Mol. Cell. Biol.* 8: 963-973 (1988).

Horiuchi, et al., "Scavenger Function of Sinusoidal Liver Cells: Acetylated Low-density Lipoprotein is Endocytosed via a Route Distinct from Formaldehyde-treated Serum Albumin", *J. Biol. Chem.* 259: 53-56 (1985).

Huang, et al., "Membrane glycoprotein IV (CD36) is physically associated with the Fyn, Ltn, anfd Yes protein-tyrosine kinases in human platelets," *Proc. Natl. Acad. Sci. USA* 88: 7844-7848 (1991).

Hunt & Calderwood, "Characterization and sequence of a mouse hsp70 gene and its expression in mouse cell lines", *Gene* 87: 199-204 (1990).

Itakura, et al., "Synthesis and use of synthetic oligonucleotides", in *Ann. Rev. Biochem.* 53: 323-356 (1984).

Joyner et al, "Production of a mutation in mouse En-2 gene by homologous recombination in embryonic stem cells," *Nature* 338: 153-156 (1989).

Kodama et al, "Type I macrophage scavenger receptor contains α-helical and collagen-like coiled coils" *Nature* 343: 531-535 (1990).

Koff, et al., "Formation and activation of a cyclin E-cdk2 complex during the G1 phase of the human cell cycle," *Science* 257: 1689-1694 (1992).

Kozarsky, et al., "Overexpression of the HDL receptor SR-B1 alters plasma HDL and bile cholesterol levels," *Nature* 387: 414-417 (1997).

Krieger, "Complementation of Mutations in the LDL Pathway of Receptor-Mediated Endocytosis by Cocultivation of LDL Receptor-Defective Hamster Cell Mutants", *Cell* 33: 413-422 (1983).

Krieger, "Molecular flypaper and atherosclerosis: structure of the macrophage scavenger receptor", *Trends Biochem. Sci.* 17:141-146 (1992).

Krieger & Herz, "Structure and Functions of Multiligand Lipoprotein Receptors: Macrophage Scavenger Receptors and LDL Receptor-Related Protein (LRP)," *Ann. Rev. Biochem.* 63: 601-637 (1994).

Landschulz, et al., "Regulation of scavenger receptor, class B, type I, a high density lipoprotein receptor, in liver and steroidogenic tissues of the rat," *J Clin Invest.* 98(4):984-95 (1996).

Lewis & Dean, "Automated site-directed drug design: the formation of molecular templates in primary structure generation", *Proc. R. Soc. Lond.*, 236:125-140 and 141-162 (1989).

Lowry, et al. "Protein Measurement with the Folin Phenol Reagent", *J. Biol. Chem.* 193: 265-275 (1951).

Maher, et al., "Inhibition of DNA Binding Proteins by Oligonucleotide-Directed Triple Helix Formation", *Science* 245:725-730 (1989).

McKinlay & Rossmann, "Rational design of antiviral agents", *Annu. Rev. Pharmacol. Toxiciol.* 29:111-122 (1989).

Merrifield, "Solid Phase Peptide Synthesis. I. The Synthesis of a Tetrapeptide", *J. Am. Chem. Soc.* 85: 2149-2154 (1963).

Miettinen, et al., "Abnormal lipoprotein metabolism and reversible female infertility in HDL receptor (SR-BI)-deficient mice," *J Clinical Invest.* 108: 1717-1722 (2001).

Moestrup, et al., "Distribution of the α2-macroglobulin receptor/low density lipoprotein receptor-related protein in human tissues", *Cell Tissue Res.* 269: 375-382 (1992).

Mulligan, "The Basic Science of Gene Therapy", *Science* 260: 926-932 (1993).

Nagelkerke, et al., "In Vivo and in Vitro Uptake and Degradation of Acetylated Low Density Lipoprotein by Rat Liver Endothelial, Kupffer, and Parenchymal Cells", *J. Biol. Chem.* 258: 12221-12227 (1983).

Naito, et al., "Tissue Distribution, Intracellular Localization, and In Vitro Expression of Bovine Macrophage Scavenger Receptors", *Am. J. Pathol* 139: 1411-1423 (1991).

Narang, et al., in "Chemical Synthesis of Deoxyoligonucleotides by the Modified Triester Method", *Methods Enzymol* 65: 610-620 (1980).

Noguchi, et al., "Inhibition of oxidation of low-density lipoprotein by a novel antioxidant, BO-653, prepared by theoretical design," *Arch. Biochem. Biophys.* 347(1): 141-147. (1997).

Ockenhouse, et al., "Activation of Monocytes and Platelets by Monoclonal Antibodies or Malaria-infected Erythrocytes Binding to the CD36 Surface Receptor in vitro", *J. Clin. Invest.* 84: 468-475 (1989).

Offensperger, et al., "In vivo inhibition of duck hepatitis B virus replication and gene expression by phosphorothioate modified antisense oligodeoxynucleotides", *EMBO J.* 12: 1257-1262 (1993).

Oquendo, et al., "CD36 Directly Mediates Cytoadherence of Plasmodium falciparium Parasitized Erythrocites", *Cell* 58: 95-101 (1989).

Orson, et al., "Oligonucleotide inhibition of IL2Rα mRNA transcription by promoter region collinear triplex formation in lymphocytes", *Nucl. Acids Res.* 19: 3435-3441 (1991).

Ottnad, et al., "Differentiation of binding sites on reconstituted hepatic scavenger receptors using oxidized low-density lipoprotein", *Biochem J.* 281: 745-751 (1992).

Perry & Davies, "The Use of 3D Modelling Databases for Identifying Structure Activity Relationships", QSAR: Quantitative Structure-Activity Relationships in Drug Design, pp. 189-193 (Alan R. Liss, Inc. 1989).

Pitas, et al., "Acetoacetylated lipoproteins used to distinguish fibroblasts from macrophages in vitro by fluorescence microscopy," *Arterioclerosis* 1: 177 (1981).

Postel, et al., "Evidence that a triplex-forming oligodeoxyribonucleotide binds to the c-myc promoter in HeLa cells, thereby reducing c-myc mRNA levels", *Proc. Natl. Acad. Sci. USA* 88:8227-8231 (1991).

Potter et al "Enhancer-dependent expression of human kappa immunoglobulin genes introduced into mouse pre-B lymphocytes by electroporation," *Proc. Natl. Acad. Sci. USA* 81: 7161 (1984).

Rigotti, et al. "Scavenger receptor BI- a cell surface receptor for high density lipoprotein," *Curr. Opin. Lipidol.* 8: 181-188 (1997).

Rigotti, et al., "Regulation by adrenocorticotropic hormone of the in vivo expression of scavenger receptor class B type I (SR-BI), a high density lipoprotein receptor, in steroidogenic cells of the murine adrenal gland," *J Biol Chem.* 271(52):33545-9 (1996).

Rigotti, et al., "A targeted mutation in the murine gene encoding the high density lipoprotein (HDL) receptor scavenger class B type I reveals its key role in HDL metabolism," *Proc. Natl. Acad. Sci. USA.* 94: 12610-12615 (1997).

Rigotti, et al., "The Class B Scavenger Receptors SR-BI and CD36 Are Receptors for Anionic Phospholipids" *J. Biol. Chem.* 270(27):16221-16224 (1995).

Ripka, "Computers picture the perfect drug", *New Scientist* 54-57 (1988).

Rohrer, et al., "Coiled-coil fibrous domains mediate ligand binding by macrophage scavenger receptor type II", *Nature* 343: 570-572 (1990).

Roush, "Antisense aims for a renaissance," *Science* 276: 1192-1193 (1997).

Rouvinen, et al., "*Computer-aided Drug Design*", *Acta Pharmaceutica Fennica*, 97:159-166 (1988).

Sarin, et al., "Inhibition of acquired immunodeficiency syndrome virus by oligodeoxynucleoside methylphosphonates", *Proc. Natl. Acad. Sci. USA* 85: 7448-7451 (1989).

Savill, et al., "Macrophaage Vitronectin Receptor, CD36, and Thrombospondin Cooperate in Recognition of Neutrophils Undergoing Programmed Cell Death", *Chest* 99: 6S-7S (suppl) (1991).

Schnitzer, et al. "Preferential Interaction of Albumin-binding Proteins, gp30 and gp18, with Conformationally Modified Albumins", *J. Biol. Chem.* 267:24544-24553 (1992).

Shaw, et al., "Modified deoxyoligonucleotides stable to exonuclease degradation in serum," *Nucleic Acids Res.*, 19:747-750 (1991).

Skolnick, et al., "From genes to protein structure and function: novel applications of computational approaches in the genomic era," *Trends in Biotech.* 18: 34-39 (2000).

Smith, et al., "The challenges of genome sequence annotation or 'the devil is in the details,'" *Nature Biotechnology* 15:1222-1223 (1997).

Southern and Berg, "Transformation of mammalian cells to antibiotic resistance with a bacterial gene under control of the SV40 early region promoter," *J. Mol. Appl. Gen.* 1: 327-341 (1982).

Sparrow, et al., "A Macrophage Receptor That Recognizes Oxidized Low Density Lipoprotein but Not Acetylated Low Density Lipoprotein", *J. Biol. Chem.* 264:2599-2604 (1989).

Spona, et al., "Inhibition of Ovulation by an oral contraceptive containing 100 μg levonorgestrel in combination with 20 μg ethinylestradiol," *Contraception* 54: 299-304 (1996).

Stanton, et al., "A Macrophage Fc Receptor for IgG Is Also a Receptor for Oxidized Low Density Lipoprotein," *J. Biol. Chem.* 267: 22446-22451 (1992).

Steinberg, et al., "Beyond Cholesterol: Modifications of Low-Density Lipoprotein That Increase Its Atherogenicity", *N. Engl. J. Med.* 320: 915-924 (1989).

Szostak, "In Vitro genetics," *TIBS* 19: 89, (1992).

Tandon, et al., "Identification of Glycoprotein IV (CD36) as a Primary Receptor for Platelet-Collagen Adhesion", *J. Biol. Chem.* 264:7576-7583 (1989).

Temel, et al., "Scavenger receptor class B, type I (SR-BI) is the major route for the delivery of high density lipoprotein cholesterol to the steroidogenic pathway in cultured mouse adrenocortical cells," *Proc Natl Acad Sci U S A.* 94(25):13600-5 (1997).

Trigatti, et al., "The role of the high-density lipoprotein receptors SR-BI in cholesterol metabolism," *Curr. Opin. Lipidol.* 11: 123-131 (2000).

Via, et al., "Identification and density dependent regulation of the AC-LDL Receptor in normal and transformed bovine aortic endothelial cells (BAEC)", *FASEB J.* 6: A371, #2135 (1992).

Whitcroft, et al., "Hormone replacement therapy: risks and benefits," *Clinical Endocrinology* 36: 15-20 (1992).

Wickstrom, et al., "Human promyelocytic leukemia HL-60 cell proliferation and c-myc protein expression are inhibited by an antisense pentadecadeoxynucleotide targeted against c-myc mRNA", *Proc. Natl. Acad. Sci. USA* 85:1028-1032 (1988).

Young, et al., "Triple helix formation inhibits transcription elongation in vitro", *Proc. Natl. Acad. Sci. USA*, 88: 10023-10026 (1991).

Zamecnik, et al., "Inhibition of *Rous sarcoma* virus replication and cell transformation by a specific oligodeoxynucleotide", *Proc. Natl. Acad. Sci. USA* 75: 280-284 (1978).

Zamecnik, et al., " Inhibition of replication and expression of human T-cell lymphotropic virus type III in cultured cells by exogenous systhenic oligonucleotides complementary to viral RNA", *Proc. Natl. Acad. Sci.* 83: 4143-4146 (1986).

Zhu, et al., "Systemic Gene Expression After Intravenous DNA Delivery into Adult Mice," *Science* 261: 209-211 (1993).

Zimmer and Gruss, 'Production of chimaeric mice containing embryonic stem (ES) cells carrying a homoeobox Hox 1.1 allele mutated by homologous recombination,' *Nature* 338: 150-153 (1989).

\* cited by examiner

LIPID-ALTERING COMPOSITIONS FOR THE TREATMENT OF INFERTILITY

STATEMENT REGARDING FEDERALLY SPONSORED RESEARCH

The U.S. government has certain rights to this invention by virtue of Grants HL41484, HI-52212, HL20948, HL-66105, and HL-64737 from the National Institutes' of Health Heart Lung and Blood Institute.

CROSS REFERENCE TO RELATED APPLICATION

This application claims priority to U.S. Ser. No. 09/148,012 filed Sep. 4, 1998, which claims benefit of U.S. Provisional Application No. 60/057,943 filed Sep. 5, 1997.

BACKGROUND OF THE INVENTION

The present invention is generally in the area of treating infertility in females and disorders involving steroidal overproduction, such as Cushings' disease, or disorders which can be treated by lowering steroid levels, such as endometriosis and breast and prostate cancer, by altering lipid levels and uptake of cholesterol and other lipids via the SR-BI scavenger receptor.

The intercellular transport of lipids through the circulatory system requires the packaging of these hydrophobic molecules into water-soluble carriers, called lipoproteins, and the regulated targeting of these lipoproteins to appropriate tissues by receptor-mediated pathways. The most well characterized lipoprotein receptor is the LDL receptor, which binds to apolipoproteins B-100 (apoB-100) and E (apoE), which are constituents of low density lipoprotein (LDL), the principal cholesteryl-ester transporter in human plasma, very low-density lipoprotein (VLDL), a triglyceride-rich carrier synthesized by the liver, intermediate-density lipoprotein (IDL), and catabolized chylomicrons (dietary triglyceride-rich carriers).

LDL receptors and most other mammalian cell-surface receptors that mediate binding and, in some cases, the endocytosis, adhesion, or signaling exhibit two common ligand-binding characteristics: high affinity and narrow specificity. However, two additional lipoprotein receptors have been identified which are characterized by high affinity and broad specificity: the macrophage scavenger receptors class A type I and type II. Scavenger receptors mediate the endocytosis of chemically modified lipoproteins, such as acetylated LDL (AcLDL) and oxidized LDL (OxLDL), and have been implicated in the pathogenesis of atherosclerosis (Krieger and Herz, 1994 *Annu. Rev. Biochem.* 63, 601–637; Brown and Goldstein, 1983 *Annu. Rev. Biochem.* 52, 223–261; Steinberg et al., 1989 *N. Engl. J. Med.* 320, 915–924). Macrophage scavenger receptors exhibit complex binding properties, including inhibition by a wide variety of polyanions, such as maleylated BSA (M-BSA) and certain polynucleotides and polysaccharides, as well as unusual ligand-cross competition (Freeman et al., 1991 *Proc. Natl. Acad. Sci. U.S.A.* 88, 4931–4935, Krieger and Herz, 1994). Several investigators have suggested that there may be at least three different classes of such receptors expressed on mammalian macrophages, including receptors which recognize either AcLDL or OxLDL, or both of these ligands (Sparrow et al., 1989 *J. Biol. Chem.* 264, 2599–2604; Arai et al., 1989 *Biochem. Biophys. Res. Commun.* 159, 1375–1382; Nagelkerke et al., 1983 *J. Biol. Chem.* 258, 12221–12227).

Krieger, et al., in PCT/US95/07721 "Class BI and CI Scavenger Receptors" Massachusetts Institute of Technology ("Krieger, et al."), described the isolation and cloning of two distinct scavenger receptor type proteins having high affinity for modified lipoproteins and other ligands, SR-BI, an AcLDL and LDL binding scavenger receptor, which is distinct from the class A type I and type II macrophage scavenger receptors, and dSR-CI, a non-mammalian AcLDL binding scavenger receptor having high ligand affinity and broad specificity, isolated from *Drosophila melanogaster*.

Krieger, et al. reported in PCT98/18463 by Massachusetts Institute of Technology that the SR-BI receptor is expressed principally in steroidogenic tissues and liver and appears to mediate HDL-transfer and uptake of cholesterol. Competitive binding studies show that SR-BI binds LDL, modified LDL, negatively charged phospholipid, and HDL. Direct binding studies show that SR-BI expressed in mammalian cells (for example, a varient of CHO cells) binds HDL, without cellular degradation of the HDL-apoprotein, and lipid is accumulated within cells expressing the receptor. These studies indicate that SR-BI play a major role in transfer of cholesterol from peripheral tissues, via HDL, into the liver and steroidogenic tissues, and that increased or decreased expression in the liver or other tissues may be useful in regulating uptake of cholesterol by cells expressing SR-BI, thereby decreasing levels in foam cells and deposition at sites involved in atherogenesis.

Infertility is a major problem, with a multitude of causes ranging in the female from physical blockage to hormonal imbalance to unknown causes. In most cases, women are treated initially using hormones to see if fertility is improved (for example, restoration of normal menstrual cycles, pregnancy, or resolution of fibroid cysts). Surgical intervention is then usually attempted, to removed blockages or cysts. There remain many women for whom such treatments are not effective.

It is therefore an object of the present invention to provide methods and reagents for identifying pharmaceutical compositions that can alter lipid levels mediated by SR-BI and thereby restore fertility to women in need thereof.

It is a further object of the present invention to provide pharmaceutical compositions that can alter lipid levels mediated by SR-BI and thereby restore fertility to women in need thereof.

SUMMARY OF THE INVENTION

SR-BI is present at relatively high levels on the membranes of hepatocytes and steroidogenic tissues, including the adrenal gland, testes, and ovaries, where it mediates the uptake and transport of cholesteryl ester from high density lipoproteins. It has been demonstrated that transgenic animals which do not produce SR-BI are healthy, with the exception that the females are infertile. This provides evidence that inhibition of SR-BI activity (lipid uptake, lipid efflux, ligand binding) can be used to inhibit pregnancy. The same pathway can also be used to decrease production of steroids, and therefore be used as a therapy for disorders involving steroidal overproduction and disorders treated with drugs that decrease steroids, such as endometriosis, and breast and prostate cancer. As demonstrated by the examples, SR-BI KO females have abnormal HDLs, ovulate dysfunctional oocytes and are infertile. Surgical, genetic and pharmacologic methods were used to show that the fertility of SR-BI KO females (or their transplanted oocytes) can be restored in the absence of ovarian and/or extraovarian SR-BI expression by manipulations that modify the structure, composition and/or abundance of their abnormal plasma lipoproteins. These manipulations included inactivation of the apolipoprotein A-I gene and administration of the cholesterol-lowering drug PROBUCOL™. In the absence of treatment, female animals which do not express SR-BI have dramatically reduced levels of offspring, even though they are otherwise healthy and the males normal. Studies demonstrate that they do not produce viable eggs and have a defect involving development and viability of fertilized eggs. These studies provided the novel and unexpected insight that manipulation of lipoprotein metabolism can influence (inhibit or restore) female fertility

BRIEF DESCRIPTION OF THE DRAWINGS

FIG. 2A is a graph of fertility expressed as percentage of females producing litters. FIG. 2B is a graph of the average number of pups delivered per month per female mated (error bars represent SEM).

DETAILED DESCRIPTION OF THE INVENTION

Figure 1A:
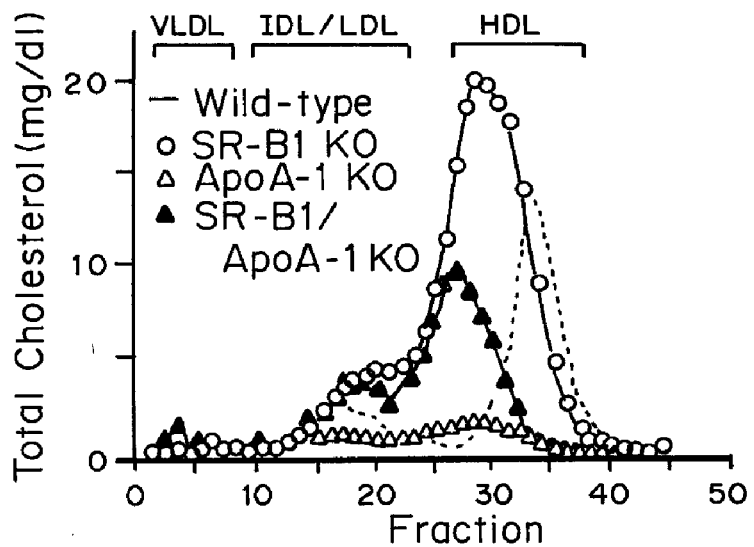
FIGS. 1a, 1b, and 1c are graphs of the effects of genctic disruption of the apoA-I gene or PROBUCOL™ treatment on plasma lipoprotein profiles of wild-type and SR-BI KO mice. Plasma lipoproteins were separated by size-exclusion chromatography (SUPEROSE™ 6-FPLC), and total cholesterol was measured for each fraction (expressed as milligrams per deciliter of plasma). Approximate elution positions of VLDL, IDL/LDL, and HDL are indicated. Lipoprotein-cholesterol profiles of (a) wild-type (dashed line, pooled plasma from four mice): SR-BI KO mice (open circles, pooled plasma from seven mice); apoA-I KO mice (open triangles, pooled plasma from three mice); and SR-BI/apoA-I double-KO mice (filled triangles; average of three chromatograms from three mice) (FIG. 1A); (b) wild-type mice fed first with normal chow (open squares, pooled plasma from four mice, same as dashes in a); then with 0.5% PROBUCOL™-enriched chow for 11 days (filled squares, pooled plasma from four mice) FIG. 1B); and (c) SR-BI KO mice fed first with normal chow (open circles, pooled plasma from seven mice, same as in a); and then with 0.5% PROBUCOL™-enriched chow for 25 days (filled circles, pooled plasma from seven mice) (FIG. 1C).

Human female infertility, which in many cases is of unknown etiology, is a significant medical problem. The influence of abnormal lipoprotein metabolism on female infertility has not been thoroughly explored, despite observations suggesting a potential role for plasma lipoproteins, especially HDL. Lipoproteins transport between tissues a number of lipids (e.g., cholesterol, steroid hormones, and vitamin E) that either directly, or indirectly through their metabolic products, play key roles in fertility. In many species, including humans, the only lipoprotein detected in substantial amounts in the follicular fluid surrounding the developing oocyte in the ovary is HDL. HDL may deliver critical lipid nutrients to either the follicular cumulus cells or the oocytes for membrane synthesis, local steroid hormone production, or other processes essential for normal oocyte maturation. It might also have a role in cholesterol efflux from the oocyte/cumulus cells, thus participating in the maintenance of cellular cholesterol balance. Therefore, abnormalities in HDL metabolism affecting its structure, abundance, or function might compromise female fertility.

The role of SR-BI has now been confirmed as a principle mediator of cholesteryl ester transport from peripheral tissues via HDL directly to the liver and other steroidogenic tissues, including the adrenal gland, testes and ovaries. Western blotting has been used to show that upon estrogen treatment in rats levels of SR-BI protein drop dramatically and LDL receptor levels increase in liver. As used herein, steroidogenic tissues refer to non-placental steroidogenic tissues including adrenal, ovary and testes. The liver and non-hepatic steroidogenic tissues have been shown to be sites of selective cholesterol uptake from HDL. Fluorescently labeled HDL has been used as a marker of lipid uptake and injected into estrogen and control treated animals. Animals receiving estrogen had significantly reduced levels of SR-BI expressed in the liver, and elevated levels of SR-BI and fluorescence in the ovaries. Since administration of estrogen is associated with a number of side effects, inhibition is more preferably achieved through the use of agents which inhibit expression of SR-BI, translation of SR-BI, binding of SR-BI, or cellular processing mediated by the SR-BI. Inhibition can be direct or indirect, competitive or irreversible. Inhibition of SR-BI can thereby be used to limit steroid production in steroidogenic tissues, and serve either as a means of contraception or a means of treating disorders associated with overproduction of steroids.

Alternatively, compounds are administered with interfer with SR-BI mediated binding or uptake or transfer of lipids. As demonstrated by the examples, compounds such as probucol have been demonstrated to restore fertility in SR-BI knockout female mice, presumably through alteration of lipid levels mediated by SR-BI.

I. Pharmaceutical Compositions.

A number of compounds are useful in altering lipid levels and cholesterol metabolism for use in treating infertility and related lipid disorders. A preferred class of compounds are PROBUCOL™ (4,4'-(isopropylidenedithio) bis(2,6-di-tert-butylphenol)) and monoesters of PROBUCOL™, for example, as described in U.S. Pat. No. 6,121,319 to Somers and other derivatives as described by FR 2168137, FR 2140771, FR 2140769, FR 2134810, FR 2133024, and FR 2130975. These compounds have potent antioxidant properties and block oxidative modification of LDL. PROBUCOL™ has two known effects: (1) hypocholesterolemic agent (reduces plasma cholesterol, HDL and LDL in humans—side effect, causes long QT syndrome, which their esters avoid, as well as decrease in HDL) and (2) an antioxident, may also play a role in fertility.

Another useful compound available from Chugai of Japan is BO 653, 2,3-Dihydro-5-hydroxy-2,2-dipentyl-4,6-di-tert-butyl-benzofuran, an antioxidant. Noguchi, et al., Arch. Biochem. Biophys. 1:347 (1997).

Based on the PROBUCOL™ data, other compounds that will be effective include other hypocholesterolemic and antioxident compounds, including vitamin E and vitamin C, as fertility enhancing agents as well as for treatment and/or prevention of cardiovascular disease or atherosclerosis. The preferred compounds would have both activities.

Inhibitors of SR-BI can also be utilized. Direct inhibitors of SR-BI include nucleotide molecules such as antisense oligonucleotides, ribozymes, and triplex forming oligonucleotides which bind to the SR-BI gene, either the protein encoding region of the gene or the regulatory regions of the gene; small organic molecules which bind to the SR-BI protein; soluble SR-BI protein or fragments thereof which competitively bind to the substrate for cell bound SR-BI; and compounds which block binding of HDL to SR-BI.

In a preferred embodiment, these compounds are initially screened using an assay such as the assays described below and then tested in transgenic animals made using standard transgenic animal technology to knockout or overexpress the SR-BI gene. A technique such as embryonic stem cell technology using rats, mice or hamsters or the use of retroviral or adenoviral vectors is preferred, to yield animals expressing some SR-BI.

The cDNA encoding SR-BI has been cloned and is reported in Krieger, et al. The cDNA encoding SR-BI yields a predicted protein sequence of 509 amino acids which is approximately 30% identical to those of the three previously identified CD36 family members. The cloned hamster SR-BI cDNA is approximately 2.9 kb long. The sequences of the 5' untranslated region, the coding region, and a portion of the 3' untranslated region are shown in SEQ ID NO:1. The predicted protein sequence is 509 amino acids (SEQ ID NO:2) with a calculated molecular weight of 57 kD. The murine cDNA is shown in SEQ ID NO:3 and the predicted amino acid sequence is shown in SEQ ID NO:4.

As used herein, unless specifically stated otherwise, the term "SR-BI" refers to the nucleotide and amino acid sequences, respectively, shown in SEQ ID NOs:1 and 2, and 3 and 4, and degenerate variants thereof and their equivalents in other species of origin, especially human, as well as functionally equivalent variants, having additions, deletions, and substitutions of either nucleotides or amino acids which do not significantly alter the functional activity of the protein as a receptor characterized by the binding activity identified above. Studies on human SR-BI show that human SR-BI is expressed in tissues similarly to murine SR-BI and has in vitro binding activity similar to murine SR-BI.

Carriers

Compounds are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

The pharmaceutical compositions are administered in an effective amount effective to modify or treat the disorder. These are readily determined by measuring blood, urine and/or tissue samples using clinically available tests, as demonstrated below.

II. Methods of Regulation of SR-BI Cholesterol Transport to Alter Steroidogenesis and Fertility.

Compounds which alter SR-BI mediated lipid levels can be administered orally or via other routes, such as parenteral, topically, and intravaginally. Compounds may be administered one or more times daily for as long as treatment is needed. Typically treatment is not curative, but rather transitory for as long as the drug is administered. Effective dosages and treatment schedules can be readily ascertained by those skilled in the art based on known uses for the same compounds, or by extrapolation from systems such as the SR-BI transgenic mice described in Example 1.

The present invention will be further understood by reference to the following non-limiting examples.

EXAMPLE 1

Analysis of Estrogen-Treated Rat Tissues for Expression of SR-BI

Methods

Tissues of estrogen-treated rats were screened for expression of SR-BI as described above following treatment of rats with 17-α-ethylenyl estradiol (estrogen). The rats were treated for five consecutive days with subcutaneous injections of 5 mg/kg 17-α-ethylenyl estradiol in propylene glycol or with propylene glycol alone (sham-injected).

Results

Immunoblots comparing the expression of SR-BI in rat tissues in estrogen-treated or sham-treated animals show the upregulation of SR-BI in rat adrenal membranes from animals treated with estrogen as compared with controls. There is no change in SR-BI levels in tissues showing trace signal, including lung as well as testes and skin. A longer exposure, comparing a SR-BI positive control and negative control, with liver tissues from estrogen treated and sham treated animals, and adrenal tissues from estrogen treated and sham treated animals show the same results.

Immunoblots comparing expression of the SR-BI and LDL receptor show that SR-BI expression was dramatically downregulated under conditions of tremendous upregulation of the LDL-receptor.

EXAMPLE 2

Analysis of Lipid Uptake in Estrogen Treated Animals

Methods

For analysis of HDL lipid uptake in vivo, rats were anesthetized with nembutal or metafane before injection of DiI-HDL (800 μg protein/kg) into the left jugular vein. 1 hour later the anesthetized animals were perfused with oxygenated HBSS. Frozen sections (12 μm thick) of sucrose-infiltrated tissues were prepared. Tissue sections were viewed and photographed with a Zeiss photomicroscope III with the appropriate filter package.

Results

When HDL labeled fluorescently with DI, as described above, was injected into the treated and control animals, animals receiving estrogen had significantly reduced levels of SR-BI expressed in the liver, and elevated levels of SR-BI and fluorescence in the ovaries. The uptake of lipid into adrenal tissues was also dramatically increased in the estrogen-treated animals.

EXAMPLE 3

Production and Characterization of Transgenic Animals that Do Not Express SR-BI

To determine directly if SR-BI normally plays an important role in HDL metabolism in vivo and to establish an experimental system to examine the role of SR-BI in pathologic states, mice containing a targeted null mutation in the gene encoding SR-BI were generated.

Materials and Methods

Generation of SR-BI Mutant Mice.

SR-BI genomic DNA was isolated from a mouse strain 129 DNA library (Genome Systems, St. Louis, Mo.), and screened by PCR amplification using primer pairs corresponding to the 5' and 3' ends of the mSR-BI cDNA. From one clone a 12 kb Xba I fragment containing the first coding exon was identified. A replacement-type targeting vector, containing 0.75 kb and 9 kb short and long homology regions and the pol2sneobpA and herpes simplex virus thymidine kinase (TK) cassettes, was constructed using standard methods. The vector was linearized and 100 μg were transfected by electroporation (240 V, 500 μF) into $112 \times 10^6$ murine D3 embryonic stem cells, which were then plated onto irradiated mouse embryonic fibroblast feeder layers. After G418/gancyclovir positive/negative selection for 7–8 days, 492 of the 5800 surviving colonies were picked and screened by PCR analysis using primers specific for the targeted allele (primer 15'-

```
TGAAGGTGGTCTTCAAGAGCAGTCCT-3';    (SEQ ID NO:5)
and
primer 3
5'-GATTGGGAAGACAATAGCAGGCATGC-3'; (SEQ ID NO:6)
all
``` oligonucleotide primers were synthesized by Research Genetics). The presence of the targeted allele (amplification of a 1.4 kb band) was confirmed by Southern blot analysis of Xba I digested genomic DNA using probes that yielded either the predicted 12 kb fragment characteristic of the wild-type allele or the predicted 2.5 kb and 9 kb fragments from the targeted mutant allele. Bam HI digested genomic DNA was also probed with a 0.9 kb fragment derived by Pst I digestion of the neomycin resistance gene cassette to confirm the presence of a single neo gene in the mutant cells. Embryonic stem cell clones containing a disrupted SR-BI allele were injected into C57BL/6 blastocysts, which were implanted into recipient females. The resulting chimeric mice were crossed to C57BL/6 female mice to generate F1 wild-type (srbI$^{+/+}$) and heterozygous (srbI+/$^{+-}$) mice on an identical 129 (agouti)/C57BL/6 background. F1 heterozygotes were crossed to generate F2 wild-type (srbI$^{+/+}$), heterozygous mutant (srbI$^{+/-}$) and homozygous mutant (srbI$^{+/-}$) progeny. The presence of the targeted or wild-type SR-BI alleles in DNA extracted from tail biopsies was detected by PCR amplification using primer 1 in combination with either primer 3 (mutant specific) or primer 2 (wild-type specific; 5'-TATCCTCGGCAGACCTGAGTCGTGT-3' (SEQ ID NO:7)). Genotypes were confirmed by Southern blot analysis. Mice were housed in microisolator cages and were fed ad libitum a regular rodent chow diet (Prolab 3000, PMI Feeds Inc., St. Louis, Mo.).

Analysis of animal tissues:

Samples were obtained from fasted (4–8 hrs) or non-fasted mice that were approximately 8–12 weeks old (F1 generation) or 5–11 weeks old (F2 generation).

Immunoblot Analysis.

Animals were sacrificed and livers and adrenal glands were removed and immediately frozen. Membranes from homogenates were prepared. 50 μg of protein per specimen were analyzed by SDS-polyacrylamide (8%) gel electrophoresis and immunoblotting with chemiluminescence detection as previously described using rabbit antipeptide polyclonal antibodies which specifically recognize either the approximately 82 kDa murine SR-BI protein (anti-mSR-BI$^{485}$) or the approximately 36 kDa ε-COP control cytoplasmic protein (anti-εCOP).

Plasma and Adrenal Cholesterol Analysis.

Plasma total cholesterol (unesterified plus esterified, mg/dl) was measured using an enzymatic kit (Sigma Chemicals, St. Louis, Mo.). Adrenal glands were homogenized as described above. Protein concentrations in the homogenates were measured using the method of Lowry et al. Duplicate samples of homogenates (30–70 μl each) were extracted with 2 ml of hexane/isopropanol (2:1) for 1 h at room temperature, back-washed with 1 ml of water, and phases separated by centrifugation at 800×g for 5 min. The upper organic phase was recovered and evaporated at 37° C. in a Speedvac concentrator and cholesterol was measured in the dried pellet using an enzymatic kit (Sigma). Cholesterol values were corrected based on the recovery of a [$^3$H] cholesteryl ester internal standard added prior to lipid extraction. Total cholesterol content was expressed as μg of cholesterol/mg total protein.

Lipoprotein Analysis.

Pooled plasma (150 μl total from 2–6 animals) was diluted with an equal volume of elution buffer (154 mM NaCl 1 mM EDTA, pH 8) and subjected to FPLC using two Superose 6 columns (Pharmacia, Piscataway, N.J.) connected in series. Proteins were eluted at 0.25 ml/min. Forty seven fractions (0.5 ml) were collected after the first 14 ml were eluted and total cholesterol in each fraction was determined as described above. Immunoblotting of the FPLC fractions was performed with specific anti-apoA-I, anti-apoA-II or anti-apoE antibodies on independent samples or by sequential labeling of a single membrane to permit simultaneous visualization of all three proteins.

Statistical Analysis.

Results are expressed as the arithmetic mean±standard deviation. The statistical significance of the differences of the mean between groups was evaluated using the Student t test for unpaired comparisons. The $\chi^2$ test was used for genotype distribution analysis. P values<0.05 are considered to be statistically significant.

Results and Discussion

The SR-BI gene was inactivated in embryonic stem cells by standard homologous recombination methods. The segments replaced in the recombined mutant ("Targeted Allele") include the entire coding region of the first coding exon (126 bp, 42 amino acids, containing 5' untranslated sequence, a short N-terminal cytoplasmic domain, and a portion of the N-terminal putative transmembrance domain that probably also functions as an uncleaved leader sequence for insertion into the ER during biogenesis) and an additional 554 bases of the adjacent downstream intron. The mutated locus is expected to encode a transcript which would not be translated or would be translated into non-functional, non-membranous, and presumably unstable, protein. Two sets of primer pairs specific for the wild-type (primers 1 and 2) or targeted mutant (primers 1 and 3) alleles were used to screen genomic DNA by PCR. Immunoblot analysis of hepatic membranes from unfasted wild-type (F1 and F2 generations), heterozygous (F1 and F2 generations) and homozygous mutant (F2 generation) male mice were performed using polyclonal antipeptide antibodies to SR-BI or the internal control $\epsilon$-COP (approximately 36 kDa). Essentially identical results were obtained using specimens from female mice.

Three independently derived embryonic stem cell clones containing the targeted allele were injected into C57BL/6 blastocysts and two produced 24 male chimeras, of which 11 gave germ line transmission of the targeted SR-BI allele when crossed to C57BL/6 females. F1 offspring were either homozygous (+/+) for the wild type allele or heterozygous (+/−) with both mutant and wild-type PCR products. F1 heterozygotes should be isogenic with the F1 wild-type controls except at the SR-BI locus. Wild-type, heterozygous and homozygous mutant F2 generation offspring, whose phenotypes are subject to genetic background variability, were generated from F1 intercrosses. In the F2 progeny analyzed to date (n=317), the observed ratios of wild-type heterozygous mutant homozygous mutant offspring were 1.0:1.7:0.5, values significantly different from the expected Mendelian ratio of 1:2:1 (p=0.003). Thus, there may be partially penetrant effects of the mutation either on neonatal survival or on embryonic development, which would be consistent with the distribution of SR-BI on the maternal surfaces of cells in the placenta and yolk sac during embryonic development.

All of the mutants looked normal (weight, general appearance and behavior) and the males were fertile. No offspring from female homozygous mutants have been obtained following multiple attempts to do so, indicating a substantial, and possibly complete, decrease in fertility in these females. Immunoblot analysis of liver membranes from F1 (+/+,+/−) and F2 (+/+,+/−,−/−) mice using anti-peptide antibodies which recognize the C-terminus of the SR-BI protein (anti-mSR-BI$^{495}$), or a segment of the putative extracellular loop (anti-mSR-BI$^{230}$), revealed that there was about half as much mSR-BI protein in the heterozygous mutants as in the wild-type controls and no detectable SR-BI in the homozygous mutants. No fragment or other variants of the full-length protein were detected in any of the samples. In contrast, no significant differences were observed in the levels of the control protein, $\epsilon$-COP. Similar results were observed using adrenal tissue. Thus, the mutated SR-BI gene is a functionally null allele.

To determine how decreased SR-BI protein expression influenced lipoprotein metabolism, the plasma cholesterol levels in male and female wild-type and mutant mice were compared. Because there were no statistically significant differences between the data from animals derived from the two independent embryonic stem cell clones, data from these two independent sets of animals were pooled. Relative to wild-type controls there were statistically significant increases in the plasma total cholesterol concentrations of approximately 30–40% in F1 and F2 heterozygotes and 2.2-fold in F2 homozygous mutants. In contrast to the increased plasma cholesterol in the mutants, there was no statistically significant change in the levels of plasma apoA-I. These findings are consistent with the suggestion that hepatic SR-BI plays a key role in selective removal of cholesterol from circulating HDL-lower levels of hepatic SR-BI were expected to increase plasma HDL cholesterol but not directly alter apoA-I levels.

To determine if the elevated levels of plasma cholesterol in the mutants were due to changes in HDL, pooled plasma samples from F1 male and female and F2 male animals were subjected to FPLC and the total cholesterol content as well as the relative amounts of apoA-I, apoA-II and apoE in each fraction were measured. For wild-type mice (srbI$^{+/+}$) most of the cholesterol, apoA-I and apoA-II were in the HDL fraction, with small or undetectable amounts in the VLDL and IDL/LDL fractions. There was an apparently low level of apoE which both co-migrated with the HDL and with a small cholesterol peak in the IDL/LDL region. The cholesterol and apolipoprotein profiles of the heterozygous mutants were similar to those of the wild-type controls, except that there was an increase in the amount of cholesterol in the HDL fractions and there was a tendency of the HDL peak (cholesterol and/or apolipoproteins) to be broader than that of wild-type and shifted slightly to the left (lower fraction number, greater apparent size), which may represent large HDL particles. This suggested that there might be a difference in the average sizes of the HDL particles due to the inactivation of one of the SR-BI alleles; however, this shift was not observed in all specimens. In the F2 homozygous mutant animals (srbI$^{-/-}$) the cholesterol was found in a large, somewhat heterogeneous peak in the HDL range, but shifted to the left (larger apparent size) of the wild-type HDL peak. The amount of cholesterol in the IDL/LDL fraction varied between samples.

Combined immunoblot analysis were performed with polyclonal antibodies to apoE, apoA-I and apoAII. Additional analysis of these and independent chromatograms established that there were no additional peaks containing apoA-I in fractions containing larger lipoproteins (fractions 1–22) and that the only other peak containing a small amount of apoE was in fraction 6, which corresponds to VLDL. The distributions of apoA-I and apoA-II were similar to that of cholesterol, although, unlike the case for apoA-I there was a notable reduction in the amount of apoA-II relative to that seen in wild type and heterozygous mutant animals. Conversely, in the homozygous mutants there was a substantial increase in the amount of apoE, whose distribution profile (larger particles, centered around fractions 26–28) differed from, but overlapped, those of apoA-I and apoA-II.

These results with the mutant animals, in which the changes in SR-BI expression are in the physiologic range, are complementary to and consistent with the observation that transient adenovirus-mediated hepatic SR-BI overexpression results in dramatically decreased levels of HDL cholesterol and increased delivery of HDL-associated lipid to hepatocytes and the bile. In rodents, most of the plasma HDL cholesterol appears to be removed by the liver via selective uptake and the liver appears to be the site of the highest total amount of SR-BI protein expression. It seems likely that buildup of large, cholesterol-enriched lipoprotein particles in the circulation of SR-BI mutants was primarily due to decreased hepatic selective HDL cholesterol uptake. Thus, it appears that murine plasma HDL cholesterol levels are particularly sensitive to physiologically relevant changes in the levels of hepatic SR-BI protein expression (e.g., approximately 50% reduction in heterozygotes). The effect of the null mutation in SR-BI on total plasma cholesterol levels was quantitatively similar to that of a null mutation in the LDL receptor. For both sets of mutants, total plasma cholesterol levels were approximately 36% above wild-type controls for heterozygotes and approximately 114% for homozygotes. It is important to emphasize that while the magnitudes of the effects on total plasma cholesterol of these distinct mutations (SR-BI vs. LDL receptor) are similar, the mechanistic consequences on lipoprotein metabolism (e.g., effects on the various lipoproteins) differ.

In addition to playing an important role in regulating plasma HDL cholesterol, SR-BI has been implicated in the delivery of HDL cholesterol to the adrenal gland and other steroidogenic tissues, both for the accumulation of esterified cholesterol stores and for steroid hormone synthesis. To examine this, the cholesterol content of adrenal glands in mutant and wild-type mice was measured. The results are shown in Table 1. As predicted, cholesterol stores in the adrenal gland dropped substantially in the heterozygous and homozygous mutants to 58% and 28% of control, respectively. It was also noted that the color of intact adrenal glands from homozygous mutants was brownish-red while that of wild-type and heterozygous animals was light yellow and, in preliminary studies, a dramatic decrease in oil red O staining of the adrenal cortex was observed in the homozygous mutants relative to the wild-type mice. Thus, the total cholesterol content, color and oil red O staining characteristics of the adrenal glands in SR-BI homozygous mutants resembled those in their cholesterol-depleted counterparts in other murine mutants, including null mutants in the SR-BI ligand apoA-I. This similarity with apoA-I knockouts is consistent with the possibility that the reduction in adrenal cholesterol in the SR-BI homozygotes is a direct consequence of the loss of the key receptor for selective lipid uptake. Antibody blocking experiments have provided additional support for a major role of mSR-BI in delivering HDL cholesterol to cultured adrenocortical cells for steroidogenesis. Based on the tissue distribution and hormonal regulation of SR-BI protein expression and the phenotypes of apoA-I knockouts, it seems likely that there would also be reductions in cholesterol stores in other steroidogenic tissues (e.g., ovary, testes) in SR-BI homozygous mutants. Adrenal cholesterol deficiency in both the apoA-I and SR-BI homozygous mutants also suggests that LDL receptors in the mouse, in which there normally is little LDL in the plasma, do not normally contribute significantly to murine adrenal cholesterol accumulation.

TABLE 1

EFFECTS OF DISRUPTION OF THE GENE ENCODING SR-BI ON PLASMA TOTAL CHOLESTEROL AND APO A-I CONCENTRATIONS, AND ADRENAL GLAND TOTAL CHOLESTEROL CONTENT IN WILD-TYPE (srbI[+/+]), AND HETEROZYGOUS (srbI[+/+]), AND HOMOZYGOUS (srbI[+/+]) MUTANT MICE.

| | | F1 Generation | | | | F2 Generation | | | |
|---|---|---|---|---|---|---|---|---|---|
| srbI genotype | gender | Plasma Total Cholesterol mg/dl | % of control | Plasma Total Cholesterol mg/dl | % of control | Plasma ApoA-I mg/dl | % of control | Adrenal Gland Total Cholesterol µ/mg protein | % of control |
| +/+ | male | 93 ± 8 (29) | 100 | 99 ± 12 (18) | 100 | | | | |
| | female | 80 ± 7 (13) | 100 | 94 ± 20 (27) | 100 | — | — | — | — |
| | Both | 89 ± 10 (42) | 100 | 96 ± 17 (45) | 100 | 25 ± 3 (10) | 100 | 128 ± 28 (5) | 100 |
| +/− | male | 126 ± 10 (21) | 100 | 137 ± 21 (29) | 100 | — | — | — | — |
| | female | 112 ± 9 (23) | 140 | 118 ± 9 (49) | 112 | — | — | — | — |
| | Both | 126 ± 12 (44) | 134 | 126 ± 22 (78) | 131 | 28 ± 2 (12) | 112 | 74 ± 18 (6) | 58 |
| −/− | male | — | — | 220 ± 41 (10) | 222 | — | — | — | — |
| | female | — | — | 209 ± 32 (7) | 222 | — | — | — | — |
| | Both | — | — | 216 ± 37 (17) | 225 | 27 ± 3 (11) | | 36 ± 7 (5) | 28 |

Values for F1 generation represent mean ± standard deviation.
Values for F2 generation in parenthesis represent the numbers of animals analyzed.
Values for plasma total cholesterol determined with an Autoanalyzer and human apoA-I standards.
F1 generation animals were not fasted.
F2 generation animals were not fasted prior to analysis of adrenal gland cholesterol levels but were fasted for 4–8 h prior to analysis of plasma.

EXAMPLE 4

Reproductive Studies with SR-BI Knockout Mice

The female homozygous knockout mice are infertile. Several studies were conducted to determine why. These animal do exhibit estrus and ovulate. However, examination of the eggs shows them not to be viable, and to be extremely fragile, with eggs isolated after mating, at the one, two or four cell stage dying with 24 hours.

Additional studies have been conducted to look at implantation. Females were mated with vasectomized males, then implanted with normal wild type embryos. At mid-gestation, the majority of wild type controls show implantation; none of the knockout females show implantation. Preliminary studies indicate that the homozygous females have a defect in the decidual reaction.

EXAMPLE 5

Restoration of Fertility in Knockout Animals by Treatment with Probucol

Mice with homozygous null mutations in the gene for the HDL receptor SR-BI (SR-BI KO) provide an opportunity to explore the potential role of abnormal lipoprotein metabolism in infertility. Female, but not male, SR-BI KO mice are infertile, even though they exhibit normal estrus cycles, ovulation, and progesterone levels during pseudopregnancy. This infertility is due, at least in part, to the ovulation of dysfunctional oocytes. Because SR-BI is normally expressed in the uterus in the decidual cells that nourish the implanted embryo and its expression in mammary glands is stimulated in rodents by pregnancy (Landschulz, et al. 1996

J. Clin. Invest. 98:984–995) it is possible that fertility and nursing might in part depend on SR-BI expression at extraovarian sites. Genetic, surgical, and pharmacologic methods were used to study the infertility of SR-BI KO mice and report that lipoproteins can play a critical role in murine fertility. Mammalian female fertility depends on complex interactions between the ovary and the extraovarian environment (e.g., the hypothalamic-hypophyseal ovarian axis). The role of plasma lipoproteins in fertility was examined using HDL-receptor SR-BI knockout (KO) mice. SR-BI KO females have abnormal HDLs, ovulate dysfunctional oocytes, and are infertile. Fertility was restored when the structure and/or quantity of abnormal HDL was altered by inactivating the apoAI gene or administering the cholesterol-lowering drug PROBUCOL™. This suggests that abnormal lipoprotein metabolism can cause murine infertility—implying a functional hepatic-ovarian axis—and may contribute to some forms of human female infertility.

Methods

Lipoprotein analysis. Plasma, collected from Avertin anesthetized mice, was size fractionated by FPLC, and the total cholesterol in each fraction or in unfractionated plasma was determined as described previously (Rigotti, A., et al. 1997 Proc. Natl. Acad. Sci. USA. 94:12610–12615) or by using a commercial kit (Wako Chemical USA Inc., Richmond, Va., USA). For apoA-I KO mice, 500 µl of pooled plasma was used for FPLC analyses.

Animals. Mice were housed and fed a normal chow diet (19) or chow (Teklad 7001) supplemented with 0.5% (wt/wt) 4,4'-(isopropylidene-dithio)-bis-(2,6-di-tertbutylphenol (PROBUCOL™; Sigma Chemical Co., St. Louis, Mo., USA). After ovary transplant surgery, the drinking water for RAG-2-deficient mice was supplemented with the antibiotics sulfamethoxazole (1.0 mg/ml) and trimethoprim (0.2 mg/ml) (Sulfatrim pediatrics; Alpharma U.S. Pharmaceuticals Division, Baltimore, Md., USA) to prevent postoperative infections. Mouse strains (genetic backgrounds) were: wild-type and SR-BI KO (both 1:1 mixed C57BL/6×129 backgrounds; Trigatti, et al., Curr. Opinl Lipidol. 11:123-131 (2000)), apoA-I KO (Kozarsky, et al., Nature 387414–417 (1997)) (C57BL/6; The Jackson Laboratory, Bar Harbor, Me., USA), and RAG-2 KO (mixed C57BL/6×129×BALB/c background; gift from Jianzhu Chen, Massachusetts Institute of Technology). Double SR-BI/apoA-I KO and SR-BI/RAG-2 KO mice were produced by (a) mating SR-BI KO males with apoA-I KO or RAG-2-KO females, (b) transferring the resulting embryos into Swiss Webster recipients, and (c) intercrossing the double heterozygous offspring.

Colonies were maintained by crossing double- KO males with females heterozygous for the SR-BI null mutation and homozygous for the apoA-I or RAG-2 mutation to optimize the low yield of SR-BI homozygotes. It has been possible to obtain only a few homozygous null SR-BI KO mice on an essentially pure C57BL/6 background (backcrossed nine times to pure C57BL/6 mice). Experiments with these (n=3; 4- month matings, no litters) and additional mixed background SR-BI KO mice (n=19) confirmed the extremely low fertility of female SR-BI KO mice. PCR was used for genotyping the various mutant mouse lines. The primers for analyses were as follows: for SR-BI, the primers were as described by Rigotti, et al., Proc. Natl. Acad. Sci. USA 94:12610–12615 (1997); for apoA-I, the following set of four primers were used: 5' -cttgggtggagaggctattc-3' (SEQ ID NO:8), 5'-aggtgagatgacaggagatc-3'(SEQ ID NO:9), 5'-catctcgcacctttagccat-3' (SEQ ID NO:10), and 5'-tctctgt-gcccaggaaggta-3 (SEQ ID NO:11)' (sequences and protocols originally from the Jackson Laboratories), or primers 5'-ac-ccagactgtcggagagct-3" (SEQ ID NO: 12) and 5'-catcttgct-gccatacgtgc-3'(SEQ ID NO:13); and for RAG-2, the primers were 5'-agcctgcttattgtctcctg-3"(SEQ ID NO:14) and 5'-ggcaccggacaggtcggtcttgac-3" (SEQ ID NO:15) (kindly provided by Charles Whitehurst, Massachusetts Institute of Technology). All animal studies were approved by the Massachusetts Institute of Technology Committee on Animal Care. To test the fertility of genetically, surgically, or pharmacologically manipulated female mice, virgin females were housed continuously with wild-type males, and numbers of litters and pups were counted during the mating period. When the females exhibited very little or considerably reduced fertility (i.e., SR-BI KO, double SR-BI/apoA-I KO, and double SR-BI/RAG-2 KO mice), the matings were conducted for 4 months. Otherwise shorter 1- to 2-month mating periods were used when the fertile females produced litters relatively quickly.

Ovary transplantation. Donor SR-BI KO or control wild-type mice (5–6 weeks of age) were sacrificed by cervical dislocation, and the ovaries were removed. Hosts (RAG-2 KO mice), 4–6 weeks of age, were anesthetized with 2.5% Avertin (intraperitoneally), and ovary transfer surgery was performed. In brief, ovaries of the host mice were removed from the surrounding ovarian bursa by cutting the side opposite to the ovarian hilus. Ovaries from the donor mice were then inserted into the ovarian bursa and the bursa closed with Vetbond tissue adhesive (3M Animal Care Products, St. Paul, Minn., USA). In sham ovary transplants (n=5), ovaries of SR-BI KO mice were removed and reinserted into the same mouse (either unilaterally when the contralateral oviduct was cut, n=1, or bilaterally, n=4). The transplanted hosts were mated with wild-type males 2–3 weeks after surgery and the offspring genotyped by PCR as described above.

Results

SR-BI expression in the liver is crucial for normal murine lipoprotein metabolism. It extracts cholesterol (as cholesteryl esters) from the hydrophobic cores of circulating plasma HDLs (and other lipoproteins) by a selective uptake pathway. The effects of genetic disruption of the apoA-I gene or PROBUCOL™ treatment on plasma lipoprotein profiles of wild-type and SR-BI KO mice were measured and the results shown in FIG. 1. Plasma lipoproteins were separated by size-exclusion chromatography (SUPHEROSE™ 6-FPLC), and total cholesterol was measured for each fraction (expressed as milligrams per deciliter of plasma). Approximate elution positions of VLDL, IDL/LDL, and HDL are indicated. Lipoprotein-cholesterol profiles of (FIG. 1a) wild-type (dashed line, pooled plasma from four mice); SR-BI KO mice (open circles, pooled plasma from seven mice); apoA-I KO mice (open triangles, pooled plasma from three mice); and SR-BI/apoA-I double-KO mice (filled triangles; average of three chromatograms from three mice); (b) wild-type mice fed first with normal chow (open squares, pooled plasma from four mice, same as dashes in a); then with 0.5% PROBUCOL™-enriched chow for 11 days (filled squares, pooled plasma from four mice); and (c) SR-BI KO mice fed first with normal chow (open circles, pooled plasma from seven mice, same as in a); and then with 0.5% PROBUCOL™-enriched chow for 25 days (filled circles, pooled plasma from seven mice). The average plasma total cholesterol levels (±SEM) were: wild-type, 103.4±3.8 mg/dl (n=7); SR-BI KO, 211.5±6.2 mg/dl (n=13);

apoA-I KO, 25±1.2 mg/dl (n=3); SR-BI/apoA-I KO, 105.3±19.2 mg/dl (n=3); PROBUCOL™-fed wild-type, 33.6±3.4 mg/dl (n=9); PROBUCOL™-fed SR-BI KO, 107.8±6.3 mg/dl (n=14). All total cholesterol differences greater than 10 mg/dl were statistically significant (P<0.05).

In SR-BI KO mice there are abnormally high (approximately twofold) levels of plasma total cholesterol, most of which is found in abnormally large, heterogeneous, apoE-enriched HDL-like particles. This can be seen in the lipoprotein cholesterol profiles in FIG. 1. In these experiments, murine plasma samples were size fractionated (largest lipoprotein particles elute first: VLDL>IDL>LDL>HDL), and the cholesterol content of each fraction was measured. In wild-type females (FIG. 1a, dashed line) most of the cholesterol is in normal-size HDL, while in SR-BI KO females FIG. 1a, open circles) much of the cholesterol elutes earlier in abnormally large HDL particles. To determine if the abnormal HDLs in SR-BI KO females play a role in their infertility, genetic and pharmacologic methods were used to modify the structure of HDL and lower the amount of plasma HDL cholesterol in these animals, then subsequently their fertility examined by mating them with wild-type males. SR-BI KO mice were first crossed with mice that cannot synthesize apoA-I (apoA-I KO mice, the major, but not the only, protein component of the HDLs in both wild-type and SR-BI KO mice.

Figure 1B:
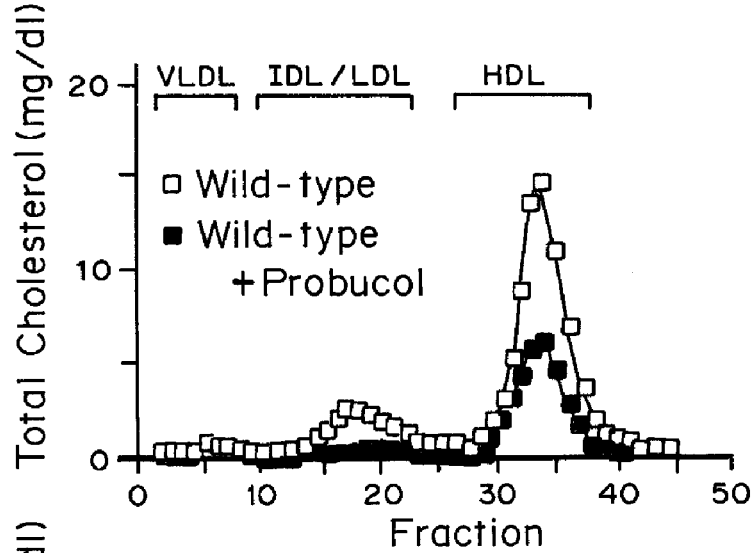
Figure 1C:
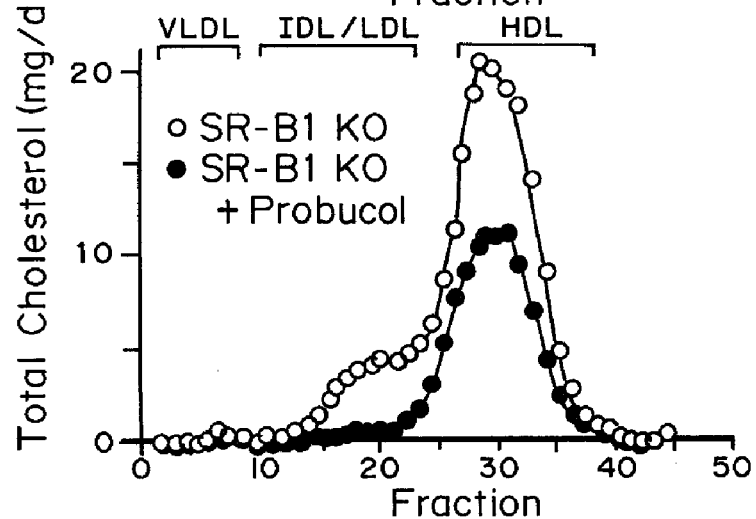

ApoA-I itself is not required for fertility. The lipid and apolipoprotein compositions of HDL in apoA-I KO mice differ from those in wild-type mice (e.g., increased apoE in the HDLs of apoA-I KO mice). These mice have a low level of plasma cholesterol, the bulk of which is HDL of somewhat larger size than normal HDL (FIG. 1a, open triangles). There was a substantial increase in the amount of large, HDL-like cholesterol in the SR-BI/apoA-I double-KO mice (FIG. 1a, filled triangles) relative to that in the apoA-I KO mice. This suggests that SR-BI participates directly in the clearance of cholesterol from apoA-I-deficient HDL. It also suggests that, even though there is only a relatively small lipoprotein cholesterol pool in apoA-I KO mice, there is nevertheless a substantial, SRBI-dependent flux of cholesterol through this pool.

Consistent with this possibility are earlier studies that showed that (a) other apolipoproteins found in HDL (e.g., apoA-II) can serve as ligands for SR-BI; and (b) adenovirus-mediated overexpression of SR-BI in apoA-I KO mice results in the loss of virtually all of the apoA-I-deficient HDL cholesterol. There was a reduction in the amount of HDL-like cholesterol in the SR-BI/apoA-I double-KO relative to SR-BI KO (FIG. 1a, open circles) mice, with the greatest reduction seen in the smallest, normal-sized HDL particles (fractions 29–38). Therefore, in the context of a SR-BI KO background, the loss of apoA-I resulted in significant changes in the structure of the HDL (e.g., no apoA-I, altered size distribution) and the amount of HDL cholesterol.

Virgin SR-BI/apoA-I double-KO females (approximately 6–8 weeks of age) were mated with wild-type males for 4 months, and pregnancies and litter sizes counted. During the 4-month mating period, 41% (7 of 17) became pregnant and carried their litters to term (FIG. 2, dark gray bars). Observed litter size varied from one to four (average 2.2), and pups from the litters of three or more were nursed properly (smaller litters were cannibalized), developed normally, and had the expected genotypes. The time of mating for the first litter to be born varied from 21 days to 3.5 months (average 56±12 days). These results establish that SR-BI is not absolutely required either in the ovaries or extraovarian tissues for successful pregnancies, provided that the extraovarian environment is appropriate (e.g., apoA-I-deficient).

Figure 2A:
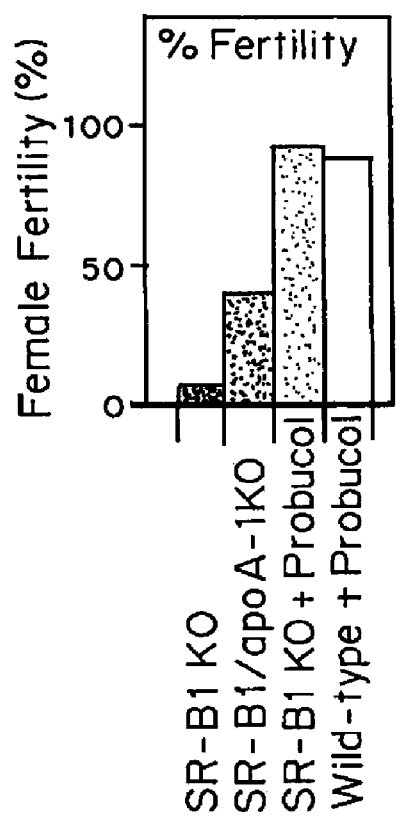
FIGS. 2a and 2b are graphs of the effects of genetic disruption of the apoA-I gene or PROBUCOL™ treatment on the fertility of female SR-BI KO mice. Wild-type males were mated with female SR-BI KO (n=13, black bars, average litter size=1, 2- to 6-month mating), SR-BI/apoA-I KO (n=17, dark gray bars, average litter size=2.2, 4-month mating), PROBUCOL™-fed SR-BI KO (n=14, light gray bars, average litter size=5.7, 1- to 2-month mating), and PROBUCOL™-fed wild-type (n=9, white bars, average litter size=5.3. 1- to 2-month mating) mice.
Figure 2B:
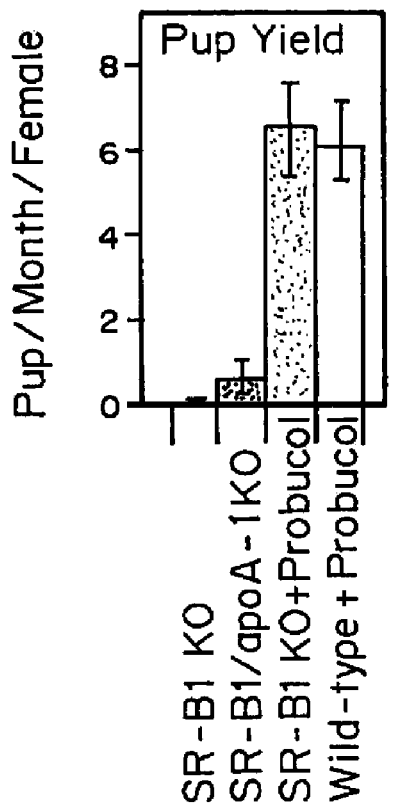

The intrinsic ability of SR-BI-deficient ovaries to produce significant levels of fertilizable oocytes was confirmed in bilateral ovary transplantation experiments in which SR-BI-negative ovaries from SR-BI KO mice were transplanted into ovariectomized SR-BI-positive hosts (n=7). Immunocompromised RAG-2 KO mice were used as hosts to minimize host-versus-graft rejection. Lipoprotein profiles of RAG-2 KO mice, analyzed by FPLC, were virtually identical to those of wildtype mice. FIG. 2 shows the effects of genetic disruption of the apoA-I gene or PROBUCOL™treatment on the fertility of female SR-BI KO mice. Wild-type males were mated with female SR-BI KO (n=13, black bars, average litter size=1, 2- to 6-month mating), SR-BI/apoA-I KO (n=17, dark gray bars, average litter size=2.2, 4-month mating), PROBUCOL™-fed SR-BI KO (n=14, light gray bars, average litter size=5.7, 1- to 2-month mating), and PROBUCOL™-fed wild-type (n=9, white bars, average litter size=5.3, 1- to 2-month mating) mice. (a) Fertility expressed as percentage of females producing litters. (b) Average number of pups delivered per month per female mated (error bars represent SEM). After mating with wildtype males, six out of seven RAG-2 KO females with SR-BI-negative ovaries (85.7%) became pregnant and carried the pregnancies to term. The litter sizes varied from one to eight, and all offspring were heterozygous for the SR-BI mutation, confirming that the oocytes originated from the transplanted ovary. Some of the mice became pregnant immediately after being mated to the males only 2–3 weeks after the transplantation surgery. Thus, the SR-BI-negative ovaries very rapidly developed the capacity to produce functional oocytes in an SR-BI-positive environment. No pregnancies were observed during the 4-month mating period in control (sham) surgeries (n=5), thus the surgical manipulation was unlikely to have been responsible for the successful pregnancies. The possibility that the reduced immunological competence of the RAG-2 KO host mice might have potentially rescued the fertility of the SR-BI-negative ovaries was examined by generating SR-BI/RAG-2 double-KO females and mating them with wild-type males. None of the SR-BI/RAG-2 double-KO mice (plasma lipoprotein profile, analyzed by FPLC, was similar to that of the SR-BI KO mice) that were mated (n=6 for a 4-month period) had litters suggesting that reduced immunological competence was unlikely to have enhanced the fertility of SR-BI-negative ovaries transplanted into the RAG-2 KO mice. Taken together, these results confirm that ovarian expression of SR-BI is not required during embryonic development (when primordial follicles are generated) or for adult maturation and ovarian function (conversion of primordial follicles to antral follicles and ovulation) for production of functional oocytes in an appropriate extraovarian environment (e.g., SR-BI-positive or apoA-I-negative). It seems likely that apoA-I-dependent changes in the structure and/or composition of the lipoproteins in the SR-BI/apoA-I double-KO females were primarily responsible for the partial restoration of fertility. Similarly, it is tempting to speculate that either the presence of normal lipoproteins or absence of abnormal lipoproteins in the plasma of RAG-2 KO hosts was the major factor enabling the transplanted SR-BI KO ovaries to produce fertilizable oocytes in this otherwise SR-BI-positive environment. Because these animals have different mixed genetic backgrounds, it is possible that some unknown modifier alleles may have influenced fertility in these experiments. To test this independently, the effects on fertility of modifying the abnormal HDL-cholesterol in SR-BI KO mice with the powerful HDL cholesterol-lowering drug PROBUCOL™ were tested. The baseline plasma total cholesterol levels of the SR-BI KO mice were two times higher than those of the wild-type mice (SR-BI KO mice, n=13, 211.5±6.2 mg/dl; wild-type mice, n=7, 103.4±3.8 mg/dl). PROBUCOL™ treatment reduced plasma cholesterol levels by approximately 67% in wild-type (FIG. 1b) and approximately 49% in SR-BI KO (FIG. 1c) mice without substantially altering the apparent sizes of the HDLs. Thus, the as yet undefined mechanism by which lowers murine plasma cholesterol (and possibly modifies the structure of lipoproteins) does not require the expression of SR-BI. Remarkably, PROBUCOL™-treatment, which began 1–3.5 weeks before mating and continued throughout the experiment, completely restored fertility to the SR-BI KO mice, measured either as percentage of experimental females producing litters (93%, FIG. 2a, light gray bar), or as average number of pups per month delivered per female mated (FIG. 2b, light gray bar). Fertility was relatively rapidly restored by drug treatment, as seen by the brief average time from mating to delivery—28.4 days (approximately 19 days of which are accounted for by the typical time for murine gestation). PROBUCOL™ treatment was significantly more effective in restoring fertility than genetically ablating apoA-I expression (FIG. 2, compare light and dark gray bars). These data show that the infertility of SR-BI KO mice is not due to irreversible defects in embryonic or postnatal ovarian development. In addition to its lipid-lowering effects, PROBUCOL™ exhibits antioxidant and possibly other activities that might have influenced fertility. However, when the PROBUCOL™, SR-BI/apoA-I double-KO mice and ovary transfer experiments are considered together, it seems likely that abnormal lipoprotein metabolism is responsible for the infertility of SR-BI KO females and that appropriate modification of the structure/composition/abundance of the lipoproteins can restore fertility in the absence of ovarian and extraovarian SR-BI expression.

SR-BI KO females have abnormal HDLs, ovulate dysfunctional oocytes and are infertile. Surgical, genetic and pharmacologic methods restore the fertility of SR-BI KO females (or their transplanted oocytes) in the absence of ovarian and/or extraovarian SR-BI expression by manipulations that modify the structure, composition and/or abundance of their abnormal plasma lipoproteins. These manipulations included inactivation of the apolipoprotein A-I gene and administration of the cholesterol-lowering drug PROBUCOL™. Thus, it seems likely that abnormal lipoprotein metabolism is responsible for the reversible infertility of SR-BI KO females. Many strains of mutant or transgenic mice with alterations in other genes affecting adult lipoprotein metabolism (e.g., LDLR, apoE, LCAT, VLDLR, HL, PLTP, CETP, ABCA1) exhibit abnormal increases or decreases in plasma cholesterol comparable or greater in magnitude than that seen in SR-BI KO mice. However, the abnormal lipoprotein cholesterol profile of SR-BI KO mice appears to be unique. In the case of the SR-BI-negative ovaries transplanted into otherwise SR-BI-positive RAG-2 host animals, the absence of abnormal lipoproteins, presence of normal lipoproteins, or both appears likely to be the cause of the restored fertility. Alternatively SR-BI KO mice may be infertile because their abnormal lipoproteins inhibit critical ovarian functions. Reduction in the amounts of such "toxic" lipoproteins by either the removal of apoA-I by mutation or PROBUCOL™ treatment might restore fertility.

Modifications and variations of the methods and materials described herein will be obvious to those skilled in the art and are intended to be encompassed by the following claims. The teachings of the references cited herein are specifically incorporated herein.

We claim:

1. A method for treating reproductive disorders involving abnormal levels of lipids in a female mammal mediated by SR-BI activity comprising administering an effective amount of a compound altering directly or indirectly the transfer of cholesterol or cholesteryl ester from high density lipoprotein or other lipoproteins via SR-BI to liver or steroidogenic tissues to normalize the abnormal levels of lipids and thereby treat one or more symptoms of the reproductive disorder resulting from the abnormal levels of lipids.

2. The method of claim 1 wherein the compound is a hypocholesterolemic agent.

3. The method of claim 1 wherein the compounds is an antioxident.

4. The method of claim 1 comprising administering a hypocholesterolemic agent as the compound in combination with an antioxident to treat the symptoms of the reproductive disorder.

5. The method of claim 1 wherein the compound is 4,4'-(isopropylidenedithio) bis(2,6-di-tert-butylphenol)) or monoesters thereof.

6. The method of claim 1 wherein the compound is 2,3-Dihydro-5-hydroxy-2,2-dipentyl-4,6-di-tert-butyl-benzofuran.

7. The method of claim 1 wherein the compound is vitamin E or C.

8. The method of claim 1 wherein the compound alters SR-BI expression.

9. The method of claim 1 wherein the compound alters binding of SR-BI to high density lipoprotein including cholesteryl ester or other lipoproteins.

10. The method of claim 1 wherein the compound increases SR-BI expression.

11. The method of claim 1 wherein the compound decreases SR-BI binding to lipoprotein or transfer of lipid selected from the group consisting of cholesterol, its derivatives, lipid soluble vitamins, and other lipid soluble molecules.

12. The method of claim 1 wherein the compound increases SR-BI binding to lipoprotein or transfer of lipid selected from the group consisting of cholesterol, its derivatives, lipid soluble vitamins, and other lipid soluble molecules.

13. The method of claim 1 wherein the compound is administered in an amount effective to restore normal reproductive function.

14. The method of claim 1 wherein the mammal has a disorder characterized by an overproduction of steroids.

15. The method of claim 1 wherein the mammal has a disorder characterized by an underproduction of steroids.

* * * * *

UNITED STATES PATENT AND TRADEMARK OFFICE
CERTIFICATE OF CORRECTION

PATENT NO. : 7,208,467 B2
APPLICATION NO. : 10/164863
DATED : April 24, 2007
INVENTOR(S) : Monty Krieger and Helena Miettinen It is certified that error appears in the above-identified patent and that said Letters Patent is hereby corrected as shown below:

Claim 3, column 31, line 67, replace "antioxident" with --antioxidant--.
Claim 4, column 32, line 55, replace "antioxident" with --antioxidant--.

Signed and Sealed this

Twenty-first Day of August, 2007

JON W. DUDAS
*Director of the United States Patent and Trademark Office*

SEQUENCE LISTING

<160> NUMBER OF SEQ ID NOS: 15

<210> SEQ ID NO 1
<211> LENGTH: 1788
<212> TYPE: DNA
<213> ORGANISM: Cricetulus griseus
<220> FEATURE:
<221> NAME/KEY: misc_feature
<222> LOCATION: (156)..(1683)
<223> OTHER INFORMATION: Encodes amino acid sequence for the Hamster
      Scavenger Receptor Class B-I

<400> SEQUENCE: 1
gccacctgca gggctactgc tgctccggcc actgcctgag actcaccttg ctggaacgtg      60
agcctcggct tctgtcatct ctgtggcctc tgtcgcttct gtcgctgtcc cccttcagtc     120
cctgagcccc gcgagcccgg gccgcacacg cggacatggg cggcagcgcc agggcgcgct     180
gggtggcggt ggggctgggc gtcgtggggc tgctgtgcgc tgtgctcggt gtggttatga     240
tcctcgtgat gccctcgctc atcaaacagc aggtactgaa gaatgtccgc atagacccca     300
gcagcctgtc ctttgcaatg tggaaggaga tccctgtacc cttctacttg tccgtctact     360
tcttcgaggt ggtcaatccc agcgagatcc taaagggtga gaagccagta gtgcgggagc     420
gtggacccta tgtctacagg gaattcagac ataaggccaa catcaccttc aatgacaatg     480

-continued

```
atactgtgtc ctttgtggag caccgcagcc tccatttcca gccggacagg tcccacggct      540
ctgagagtga ctacattata ctgcctaaca ttctggtctt gggggggcgca gtaatgatgg      600 agagcaagtc tgcaggcctg aagctgatga tgaccttggg gctggccacc ttgggccagc      660
gtgcctttat gaaccgaaca gttggtgaga tcctgtgggg ctatgaggat cccttcgtga      720
attttatcaa caaatactta ccagacatgt tccccatcaa gggcaagttc ggcctgtttg      780
ttgagatgaa caactcagac tctgggctct tcactgtgtt cacgggcgtc cagaacttca      840
gcaagatcca cctggtggac agatggaatg ggctcagcaa ggtcaactac tggcattcag      900
agcagtgcaa catgatcaat ggcacttccg ggcagatgtg gcaccattc atgacacccc       960 agtcctcgct ggaattcttc agtccggaag cctgcaggtc tatgaagctc acctaccatg     1020
attcaggggt gtttgaaggc atccccacct atcgcttcac agcccctaaa actttgtttg     1080
ccaatgggtc tgtttaccca cccaatgaag gtttctgccc gtgccttgaa tccggcattc     1140
aaaatgtcag cacttgcagg tttggtgcac ccctgtttct gtcacaccct cacttctaca     1200
atgcagaccc tgtgctatca gaagccgttc tgggtctgaa ccctgaccca agggagcatt     1260 cttttgttcct tgacatccat ccggtcactg ggatccccat gaactgttct gtgaagttgc     1320
agataagcct ctacatcaaa gctgtcaagg gcattgggca aacagggaag atcgagcccg     1380
tggtcctccc attgctgtgg tttgagcaga gcggtgccat gggcggcgag cccctgaaca     1440
cgttctacac gcagctggtg ctgatgcccc aggtacttca gtatgtgcag tatgtgctgc     1500
tggggctggg cggcctcctg ctgctggtgc ccgtcatcta ccagttgcgc agccaggaga     1560
aatgcttttt attttggagt ggtagtaaaa agggctcgca ggataaggag gccattcagg     1620
cctactctga gtctctgatg tcaccagctg ccaagggcac ggtgctgcaa gaagccaagc     1680
tgtagggtcc caaagacacc acgagccccc ccaacctgat agcttggtca gaccagccat     1740
ccagccccta cacccgctt cttgaggact ctctcagcgg acagtcgc                   1788
```

```
<210> SEQ ID NO 2
<211> LENGTH: 509
<212> TYPE: PRT
<213> ORGANISM: Cricetulus griseus
<220> FEATURE:
<221> NAME/KEY: TRANSMEM
<222> LOCATION: (9)..(32)
<223> OTHER INFORMATION: Putative
<220> FEATURE:
<221> NAME/KEY: TRANSMEM
<222> LOCATION: (440)..(464)
<223> OTHER INFORMATION: Putative
<220> FEATURE:
<221> NAME/KEY: CARBOHYD
<222> LOCATION: (102)..(104)
<223> OTHER INFORMATION: Potential
<220> FEATURE:
<221> NAME/KEY: CARBOHYD
<222> LOCATION: (108)..(110)
<223> OTHER INFORMATION: Potential
<220> FEATURE:
<221> NAME/KEY: CARBOHYD
<222> LOCATION: (173)..(175)
<223> OTHER INFORMATION: Potential
<220> FEATURE:
<221> NAME/KEY: CARBOHYD
<222> LOCATION: (212)..(214)
<223> OTHER INFORMATION: Potential
<220> FEATURE:
<221> NAME/KEY: CARBOHYD
<222> LOCATION: (227)..(229)
<223> OTHER INFORMATION: Potential
<220> FEATURE:
<221> NAME/KEY: CARBOHYD
```

```
<222> LOCATION: (255)..(257)
<223> OTHER INFORMATION: Potential
<220> FEATURE:
<221> NAME/KEY: CARBOHYD
<222> LOCATION: (310)..(312)
<223> OTHER INFORMATION: Potential
<220> FEATURE:
<221> NAME/KEY: CARBOHYD
<222> LOCATION: (330)..(332)
<223> OTHER INFORMATION: Potential
<220> FEATURE:
<221> NAME/KEY: CARBOHYD
<222> LOCATION: (383)..(385)
<223> OTHER INFORMATION: Potential
<220> FEATURE:
<221> NAME/KEY: DISULFID
<222> LOCATION: (21)..(21)
<223> OTHER INFORMATION: Potential
<220> FEATURE:
<221> NAME/KEY: DISULFID
<222> LOCATION: (251)..(251)
<223> OTHER INFORMATION: Potential
<220> FEATURE:
<221> NAME/KEY: DISULFID
<222> LOCATION: (280)..(280)
<223> OTHER INFORMATION: Potential
<220> FEATURE:
<221> NAME/KEY: DISULFID
<222> LOCATION: (321)..(321)
<223> OTHER INFORMATION: Potential
<220> FEATURE:
<221> NAME/KEY: DISULFID
<222> LOCATION: (323)..(323)
<223> OTHER INFORMATION: Potential
<220> FEATURE:
<221> NAME/KEY: DISULFID
<222> LOCATION: (334)..(334)
<223> OTHER INFORMATION: Potential
<220> FEATURE:
<221> NAME/KEY: DISULFID
<222> LOCATION: (384)..(384)
<223> OTHER INFORMATION: Potential
<220> FEATURE:
<221> NAME/KEY: DISULFID
<222> LOCATION: (470)..(470)
<223> OTHER INFORMATION: Potential

<400> SEQUENCE: 2

Met Gly Gly Ser Ala Arg Ala Arg Trp Val Ala Val Gly Leu Gly Val
1               5                   10                  15

Val Gly Leu Leu Cys Ala Val Leu Gly Val Val Met Ile Leu Val Met
            20                  25                  30

Pro Ser Leu Ile Lys Gln Gln Val Leu Lys Asn Val Arg Ile Asp Pro
        35                  40                  45

Ser Ser Leu Ser Phe Ala Met Trp Lys Glu Ile Pro Val Pro Phe Tyr
    50                  55                  60

Leu Ser Val Tyr Phe Phe Glu Val Val Asn Pro Ser Glu Ile Leu Lys
65                  70                  75                  80

Gly Glu Lys Pro Val Val Arg Glu Arg Gly Pro Tyr Val Tyr Arg Glu
                85                  90                  95

Phe Arg His Lys Ala Asn Ile Thr Phe Asn Asp Asn Asp Thr Val Ser
            100                 105                 110

Phe Val Glu His Arg Ser Leu His Phe Gln Pro Asp Arg Ser His Gly
        115                 120                 125

Ser Glu Ser Asp Tyr Ile Ile Leu Pro Asn Ile Leu Val Leu Gly Gly
    130                 135                 140

Ala Val Met Met Glu Ser Lys Ser Ala Gly Leu Lys Leu Met Met Thr
145                 150                 155                 160
```

-continued

```
Leu Gly Leu Ala Thr Leu Gly Gln Arg Ala Phe Met Asn Arg Thr Val
                165                 170                 175
Gly Glu Ile Leu Trp Gly Tyr Glu Asp Pro Phe Val Asn Phe Ile Asn
            180                 185                 190
Lys Tyr Leu Pro Asp Met Phe Pro Ile Lys Gly Lys Phe Gly Leu Phe
        195                 200                 205
Val Glu Met Asn Asn Ser Asp Ser Gly Leu Phe Thr Val Phe Thr Gly
210                 215                 220
Val Gln Asn Phe Ser Lys Ile His Leu Val Asp Arg Trp Asn Gly Leu
225                 230                 235                 240
Ser Lys Val Asn Tyr Trp His Ser Glu Gln Cys Asn Met Ile Asn Gly
                245                 250                 255
Thr Ser Gly Gln Met Trp Ala Pro Phe Met Thr Pro Gln Ser Ser Leu
            260                 265                 270
Glu Phe Phe Ser Pro Glu Ala Cys Arg Ser Met Lys Leu Thr Tyr His
        275                 280                 285
Asp Ser Gly Val Phe Glu Gly Ile Pro Thr Tyr Arg Phe Thr Ala Pro
    290                 295                 300
Lys Thr Leu Phe Ala Asn Gly Ser Val Tyr Pro Pro Asn Glu Gly Phe
305                 310                 315                 320
Cys Pro Cys Leu Glu Ser Gly Ile Gln Asn Val Ser Thr Cys Arg Phe
                325                 330                 335
Gly Ala Pro Leu Phe Leu Ser His Pro His Phe Tyr Asn Ala Asp Pro
            340                 345                 350
Val Leu Ser Glu Ala Val Leu Gly Leu Asn Pro Asp Pro Arg Glu His
        355                 360                 365
Ser Leu Phe Leu Asp Ile His Pro Val Thr Gly Ile Pro Met Asn Cys
    370                 375                 380
Ser Val Lys Leu Gln Ile Ser Leu Tyr Ile Lys Ala Val Lys Gly Ile
385                 390                 395                 400
Gly Gln Thr Gly Lys Ile Glu Pro Val Val Leu Pro Leu Leu Trp Phe
                405                 410                 415
Glu Gln Ser Gly Ala Met Gly Gly Glu Pro Leu Asn Thr Phe Tyr Thr
            420                 425                 430
Gln Leu Val Leu Met Pro Gln Val Leu Gln Tyr Val Gln Tyr Val Leu
        435                 440                 445
Leu Gly Leu Gly Gly Leu Leu Leu Leu Val Pro Val Ile Tyr Gln Leu
    450                 455                 460
Arg Ser Gln Glu Lys Cys Phe Leu Phe Trp Ser Gly Ser Lys Lys Gly
465                 470                 475                 480
Ser Gln Asp Lys Glu Ala Ile Gln Ala Tyr Ser Glu Ser Leu Met Ser
                485                 490                 495
Pro Ala Ala Lys Gly Thr Val Leu Gln Glu Ala Lys Leu
            500                 505
```

<210> SEQ ID NO 3
<211> LENGTH: 1785
<212> TYPE: DNA
<213> ORGANISM: Mus musculus
<220> FEATURE:
<221> NAME/KEY: misc_feature
<222> LOCATION: (51)..(1577)
<223> OTHER INFORMATION: Encodes the amino acid sequence for the murine
      Scavenger Receptor Class BI

<400> SEQUENCE: 3

-continued

```
ccgtctcctt caggtcctga gccccgagag cccctt ccgc gcacgcggac atgggcggca       60
gctccagggc gcgctgggtg gccttggggt tgggcgccct ggggctgctg tttgctgcgc      120
tcggcgttgt catgatcctc atggtgccct ccctcatcaa gcagcaggtg ctcaagaatg      180
tccgcataga cccgagcagc ctgtccttcg ggatgtggaa ggagatcccc gtcccttct       240
acttgtctgt ctacttcttc gaagtggtca acccaaacga ggtcctcaac ggccagaagc      300
cagtagtccg ggagcgtgga ccctatgtct acagggagtt cagacaaaag gtcaacatca      360
ccttcaatga caacgacacc gtgtccttcg tggagaaccg cagcctccat ttccagcctg      420
acaagtcgca tggctcagag agtgactaca ttgtactgcc taacatcttg gtcctggggg      480
gctcgatatt gatggagagc aagcctgtga gcctgaagct gatgatgacc ttggcgctgg      540
tcaccatggg ccagcgtgct tttatgaacc gcacagttgg tgagatcctg tggggctatg      600
acgatccctt cgtgcatttt ctcaacacgt acctcccaga catgcttccc ataaagggca      660
aatttggcct gtttgttggg atgaacaact cgaattctgg ggtcttcact gtcttcacgg      720
gcgtccagaa tttcagcagg atccatctgg tggacaaatg gaacggactc agcaagatcg      780
attattggca ttcagagcag tgtaacatga tcaatgggac ttccgggcag atgtgggcac      840
ccttcatgac acccgaatcc tcgctggaat tcttcagccc ggaggcatgc aggtccatga      900
agctgaccta caacgaatca agggtgtttg aaggcattcc cacgtatcgc ttcacggccc      960
ccgatactct gtttgccaac gggtccgtct acccacccaa cgaaggcttc tgcccatgcc     1020
gagagtctgg cattcagaat gtcagcacct gcaggtttgg tgcgcctctg tttctctccc     1080
accccactt ttacaacgcc gaccctgtgt tgtcagaagc tgttcttggt ctgaaccta      1140
acccaaagga gcattccttg ttcctagaca tccatccggt cactgggatc ccatgaact      1200
gttctgtgaa gatgcagctg agcctctaca tcaaatctgt caagggcatc gggcaaacag     1260
ggaagatcga gccagtagtt ctgccgttgc tgtggttcga acagagcgga gcaatgggtg     1320
gcaagcccct gagcacgttc tacacgcagc tggtgctgat gccccaggtt cttcactacg     1380
cgcagtatgt gctgctgggg cttggaggcc tcctgttgct ggtgcccatc atctgccaac     1440
tgcgcagcca ggagaaatgc ttttttgtttt ggagtggtag taaaaagggc tcccaggata     1500
aggaggccat tcaggcctac tctgagtccc tgatgtcacc agctgccaag ggcacggtgc     1560
tgcaagaagc caagctatag ggtcctgaag acactataag cccccaaac ctgatagctt       1620
ggtcagacca gccacccagt ccctacaccc cgcttcttga ggactctctc agcggacagc     1680
ccaccagtgc catggcctga gccccagat gtcacacctg tccgcacgca cggcacatgg      1740
atgcccacgc atgtgcaaaa acaactcagg gaccagggac agacc                    1785
```

<210> SEQ ID NO 4
<211> LENGTH: 509
<212> TYPE: PRT
<213> ORGANISM: Mus musculus

<400> SEQUENCE: 4

```
Met Gly Gly Ser Ser Arg Ala Arg Trp Val Ala Leu Gly Leu Gly Ala
1               5                   10                  15

Leu Gly Leu Leu Phe Ala Ala Leu Gly Val Val Met Ile Leu Met Val
                20                  25                  30

Pro Ser Leu Ile Lys Gln Gln Val Leu Lys Asn Val Arg Ile Asp Pro
            35                  40                  45

Ser Ser Leu Ser Phe Gly Met Trp Lys Glu Ile Pro Val Pro Phe Tyr
        50                  55                  60
```

-continued

```
Leu Ser Val Tyr Phe Phe Glu Val Val Asn Pro Asn Glu Val Leu Asn
65                  70                  75                  80

Gly Gln Lys Pro Val Arg Glu Arg Gly Pro Tyr Val Tyr Arg Glu
                85                  90                  95

Phe Arg Gln Lys Val Asn Ile Thr Phe Asn Asp Asn Asp Thr Val Ser
               100                 105                 110

Phe Val Glu Asn Arg Ser Leu His Phe Gln Pro Asp Lys Ser His Gly
               115                 120                 125

Ser Glu Ser Asp Tyr Ile Val Leu Pro Asn Ile Leu Val Leu Gly Gly
               130                 135                 140

Ser Ile Leu Met Glu Ser Lys Pro Val Ser Leu Lys Leu Met Met Thr
145                 150                 155                 160

Leu Ala Leu Val Thr Met Gly Gln Arg Ala Phe Met Asn Arg Thr Val
               165                 170                 175

Gly Glu Ile Leu Trp Gly Tyr Asp Asp Pro Phe Val His Phe Leu Asn
               180                 185                 190

Thr Tyr Leu Pro Asp Met Leu Pro Ile Lys Gly Lys Phe Gly Leu Phe
               195                 200                 205

Val Gly Met Asn Asn Ser Asn Ser Gly Val Phe Thr Val Phe Thr Gly
               210                 215                 220

Val Gln Asn Phe Ser Arg Ile His Leu Val Asp Lys Trp Asn Gly Leu
225                 230                 235                 240

Ser Lys Ile Asp Tyr Trp His Ser Glu Gln Cys Asn Met Ile Asn Gly
               245                 250                 255

Thr Ser Gly Gln Met Trp Ala Pro Phe Met Thr Pro Glu Ser Ser Leu
               260                 265                 270

Glu Phe Phe Ser Pro Glu Ala Cys Arg Ser Met Lys Leu Thr Tyr Asn
               275                 280                 285

Glu Ser Arg Val Phe Glu Gly Ile Pro Thr Tyr Arg Phe Thr Ala Pro
               290                 295                 300

Asp Thr Leu Phe Ala Asn Gly Ser Val Tyr Pro Pro Asn Glu Gly Phe
305                 310                 315                 320

Cys Pro Cys Arg Glu Ser Gly Ile Gln Asn Val Ser Thr Cys Arg Phe
               325                 330                 335

Gly Ala Pro Leu Phe Leu Ser His Pro His Phe Tyr Asn Ala Asp Pro
               340                 345                 350

Val Leu Ser Glu Ala Val Leu Gly Leu Asn Pro Asn Pro Lys Glu His
               355                 360                 365

Ser Leu Phe Leu Asp Ile His Pro Val Thr Gly Ile Pro Met Asn Cys
370                 375                 380

Ser Val Lys Met Gln Leu Ser Leu Tyr Ile Lys Ser Val Lys Gly Ile
385                 390                 395                 400

Gly Gln Thr Gly Lys Ile Glu Pro Val Val Leu Pro Leu Leu Trp Phe
               405                 410                 415

Glu Gln Ser Gly Ala Met Gly Gly Lys Pro Leu Ser Thr Phe Tyr Thr
               420                 425                 430

Gln Leu Val Leu Met Pro Gln Val Leu His Tyr Ala Gln Tyr Val Leu
               435                 440                 445

Leu Gly Leu Gly Gly Leu Leu Leu Val Pro Ile Ile Cys Gln Leu
               450                 455                 460

Arg Ser Gln Glu Lys Cys Phe Leu Phe Trp Ser Gly Ser Lys Lys Gly
465                 470                 475                 480
```

```
Ser Gln Asp Lys Glu Ala Ile Gln Ala Tyr Ser Glu Ser Leu Met Ser
            485                 490                 495
Pro Ala Ala Lys Gly Thr Val Leu Gln Glu Ala Lys Leu
        500                 505
```

<210> SEQ ID NO 5
<211> LENGTH: 26
<212> TYPE: DNA
<213> ORGANISM: Artificial sequence
<220> FEATURE:
<223> OTHER INFORMATION: Synthetic PCR primer

<400> SEQUENCE: 5
tgaaggtggt cttcaagagc agtcct                                  26

<210> SEQ ID NO 6
<211> LENGTH: 26
<212> TYPE: DNA
<213> ORGANISM: Artificial sequence
<220> FEATURE:
<223> OTHER INFORMATION: Synthetic PCR primer

<400> SEQUENCE: 6
gattgggaag acaatagcag gcatgc                                  26

<210> SEQ ID NO 7
<211> LENGTH: 25
<212> TYPE: DNA
<213> ORGANISM: Artificial sequence
<220> FEATURE:
<223> OTHER INFORMATION: Synthetic PCR primer

<400> SEQUENCE: 7
tatcctcggc agacctgagt cgtgt                                   25

<210> SEQ ID NO 8
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 8
cttgggtgga gaggctattc                                         20

<210> SEQ ID NO 9
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 9
aggtgagatg acaggagatc                                         20

<210> SEQ ID NO 10
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 10
catctcgcac ctttagccat                                         20

```
<210> SEQ ID NO 11
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 11
tctctgtgcc caggaaggta                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 12
acccagactg tcggagagct                                              20

<210> SEQ ID NO 13
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 13
catcttgctg ccatacgtgc                                              20

<210> SEQ ID NO 14
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 14
agcctgctta ttgtctcctg                                              20

<210> SEQ ID NO 15
<211> LENGTH: 24
<212> TYPE: DNA
<213> ORGANISM: Artificial sequence
<220> FEATURE:
<223> OTHER INFORMATION: Synthetic PCR primer

<400> SEQUENCE: 15
ggcaccggac aggtcggtct tgac                                         24
```